(12) United States Patent
Kudo et al.

(10) Patent No.: US 11,401,461 B2
(45) Date of Patent: Aug. 2, 2022

(54) ZIRCONIA SINTERED BODY CONTAINING FLUORESCENT AGENT

(71) Applicant: KURARAY NORITAKE DENTAL INC., Kurashiki (JP)

(72) Inventors: Yasutaka Kudo, Aichi (JP); Makiko Kato, Aichi (JP); Koichi Okada, Okayama (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 243 days.

(21) Appl. No.: 16/635,424

(22) PCT Filed: Jul. 27, 2018

(86) PCT No.: PCT/JP2018/028323
§ 371 (c)(1),
(2) Date: Jan. 30, 2020

(87) PCT Pub. No.: WO2019/026809
PCT Pub. Date: Feb. 7, 2019

(65) Prior Publication Data
US 2021/0102116 A1    Apr. 8, 2021

(30) Foreign Application Priority Data

Jul. 31, 2017 (JP) .............................. JP2017-147544

(51) Int. Cl.
| C09K 11/02 | (2006.01) |
| A61C 13/08 | (2006.01) |
| A61C 13/083 | (2006.01) |
| A61C 13/087 | (2006.01) |
| C04B 35/488 | (2006.01) |
| C04B 35/624 | (2006.01) |
| C04B 35/64 | (2006.01) |
| C09K 11/08 | (2006.01) |

(Continued)

(52) U.S. Cl.
CPC ............ *C09K 11/02* (2013.01); *A61C 13/082* (2013.01); *A61C 13/083* (2013.01); *A61C 13/087* (2013.01); *B28B 1/00* (2013.01); *B28B 1/001* (2013.01); *B82B 3/00* (2013.01); *C04B 35/488* (2013.01); *C04B 35/624* (2013.01); *C04B 35/6303* (2013.01); *C04B 35/64* (2013.01); *C09K 11/08* (2013.01); *C09K 11/671* (2013.01); *C04B 2235/3246* (2013.01); *C04B 2235/3298* (2013.01); *C04B 2235/5454* (2013.01); *C04B 2235/6023* (2013.01); *C04B 2235/6027* (2013.01); *C04B 2235/6567* (2013.01); *C04B 2235/762* (2013.01); *C04B 2235/785* (2013.01); *C04B 2235/96* (2013.01); *C04B 2235/9646* (2013.01); *C04B 2235/9653* (2013.01)

(58) Field of Classification Search
CPC .. B82B 1/00; B82B 1/001; B82B 3/00; C09K 11/02; C09K 11/671; C09K 11/08; C04B 35/488; C04B 35/64; C04B 34/624; C04B 2235/3248; C04B 2235/5454; C04B 2235/6023; C04B 2235/762; C04B 2235/785; C04B 2235/6303; C04B 2235/96; C04B 2235/9653; C04B 2235/9646; C04B 2235/602
See application file for complete search history.

(56) References Cited

U.S. PATENT DOCUMENTS

| 2010/0003630 A1 | 1/2010 | Yamashita et al. |
| 2012/0012789 A1 | 1/2012 | Yamada et al. |

(Continued)

FOREIGN PATENT DOCUMENTS

| JP | 2000-159621 A | 6/2000 |
| JP | 2016-117618 | * 6/2016 |

(Continued)

OTHER PUBLICATIONS

Translation for JP 2016-117618, Jun. 30, 2016.*
(Continued)

*Primary Examiner* — C Melissa Koslow
(74) *Attorney, Agent, or Firm* — Oblon, McClelland, Maier & Neustadt, L.L.P.

(57) ABSTRACT

The present invention provides a zirconia sintered body containing a fluorescent agent and having excellent translucency and excellent strength. The present invention also provides a zirconia shaped body and a zirconia calcined body from which the zirconia sintered body can be obtained. The present invention relates to a zirconia sintered body comprising a fluorescent agent, wherein the zirconia sintered body comprises 4.5 to 9.0 mol % yttria, and has a crystal grain size of 180 nm or less, and a three-point flexural strength of 500 MPa or more. The present invention relates to a zirconia shaped body comprising a fluorescent agent, wherein the zirconia shaped body comprises 4.5 to 9.0 mol % yttria, and has a three-point flexural strength of 500 MPa or more after being sintered at 1,100° C. for 2 hours under ordinary pressure, and a crystal grain size of 180 nm or less after being sintered at 1,100° C. for 2 hours under ordinary pressure. The present invention relates to a zirconia calcined body comprising a fluorescent agent, wherein the zirconia calcined body comprises 4.5 to 9.0 mol % yttria, and has a three-point flexural strength of 500 MPa or more after being sintered at 1,100° C. for 2 hours under ordinary pressure, and a crystal grain size of 180 nm or less after being sintered at 1,100° C. for 2 hours under ordinary pressure.

21 Claims, No Drawings

(51) Int. Cl.
  *C09K 11/67* (2006.01)
  *C04B 35/63* (2006.01)
  *B28B 1/00* (2006.01)
  *B82B 3/00* (2006.01)

(56) References Cited

U.S. PATENT DOCUMENTS

| | | |
|---|---|---|
| 2013/0172441 A1 | 7/2013 | Takahata et al. |
| 2014/0367613 A1 | 12/2014 | Mashio et al. |
| 2016/0310245 A1 | 10/2016 | Fujisaki et al. |
| 2018/0029943 A1 | 2/2018 | Zwahlen et al. |

FOREIGN PATENT DOCUMENTS

| | | |
|---|---|---|
| JP | 2016-117618 A | 6/2016 |
| JP | 2016-540772 A | 12/2016 |
| WO | WO 2008/013099 A1 | 1/2008 |
| WO | WO 2010/110156 A1 | 9/2010 |
| WO | WO 2012/042911 A1 | 4/2012 |
| WO | WO 2013/094669 A1 | 6/2013 |
| WO | WO 2014/126034 A1 | 8/2014 |
| WO | WO 2015/084931 A1 | 6/2015 |
| WO | WO 2015/098765 A1 | 7/2015 |
| WO | WO 2016/124758 A1 | 8/2016 |

OTHER PUBLICATIONS

Extended European Search Report dated Mar. 16, 2021 in European Patent Application No. 18840387.7, 8 pages.
Flegler, A. J., et al., "Cubic yttria Stabilized Zirconia Sintering Additive Impacts: A comparative study", Science Direct, Ceramics International, vol. 40, pp. 16323-16335, Jul. 22, 2014, XP029053548.
International Search Report dated Oct. 23, 2018 in PCT/JP2018/028323 filed on Jul. 27, 2018, 2 pages.

* cited by examiner

ZIRCONIA SINTERED BODY CONTAINING FLUORESCENT AGENT

TECHNICAL FIELD

The present invention relates to a zirconia sintered body containing a fluorescent agent, among others.

BACKGROUND ART

A zirconia sintered body containing yttria has been used for dental materials such as dental prostheses. Many of such dental prostheses are produced by forming a zirconia shaped body of a desired shape, for example, a disc or prism shape, through the process of pressing zirconia particles or shaping a slurry or a composition containing zirconia particles, followed by calcination of the zirconia shaped body into a calcined body (mill blank), and subsequent sintering of the zirconia calcined body after cutting (milling) it into the shape of the desired dental prosthesis.

It is known that translucency improves when the yttria content in a zirconia sintered body exceeds 4 mol % (see, for example, Patent Literature 1). As a rule, improved translucency achieved by an increased yttria content in such a relatively high content range often comes at the expense of strength such as flexural strength. One possible way of relieving such strength decrease is to reduce the crystal grain size of the zirconia sintered body by, for example, using zirconia particles of small particle size.

Incidentally, natural human teeth have fluorescence. This is problematic in dental prostheses because a dental prosthesis, when it is not fluorescent, appears as missing as it fails to fluoresce in an ultraviolet environment, for example, such as in an amusement facility lit with blacklights. One approach to overcoming this issue is to add a fluorescent agent to the dental prosthesis. A zirconia sintered body containing a fluorescent agent is known, for example, such as that described in Patent Literature 2.

CITATION LIST

Patent Literature

Patent Literature 1: WO2015/098765
Patent Literature 2: JP 2016-540772 T

SUMMARY OF INVENTION

Technical Problem

In the course of investigations of the effect of adding a fluorescent agent to a zirconia sintered body exhibiting excellent translucency and strength with an yttria content of 4.5 to 9.0 mol % and a crystal grain size of 180 nm or less, the present inventors found that the strength seriously decreases, and the translucency decreases way below the anticipated value when the fluorescent agent is simply added to the zirconia sintered body.

It is accordingly an object of the present invention to provide a zirconia sintered body that excels in both translucency and strength despite containing a fluorescent agent. Another object of the present invention is to provide a zirconia shaped body and a zirconia calcined body from which such a zirconia sintered body can be obtained, and methods for conveniently producing these.

Solution to Problem

The present inventors conducted intensive studies to achieve the foregoing objects, and found that a novel zirconia sintered body that excels in both translucency and strength despite containing a fluorescent agent can be obtained by, for example, controlling the way the fluorescent agent is mixed. It was also found that the novel zirconia sintered body is particularly preferred as, for example, dental materials such as dental prostheses, and is highly useful not only as a dental prosthesis used for the cervical region of a tooth but as a dental prosthesis used for the occlusal surface of a posterior tooth, and the incisal region of a front tooth. The present inventors completed the present invention after further studies based on these findings.

Specifically, the present invention relates to the following [1] to [29].

[1] A zirconia sintered body comprising a fluorescent agent, wherein the zirconia sintered body comprises 4.5 to 9.0 mol % yttria, and has a crystal grain size of 180 nm or less, and a three-point flexural strength of 500 MPa or more.

[2] The zirconia sintered body according to [1], wherein the fluorescent agent contains a metallic element, and the zirconia sintered body comprises the fluorescent agent in an amount of 0.001 to 1 mass % in terms of an oxide of the metallic element relative to a mass of zirconia.

[3] The zirconia sintered body according to [1] or [2], wherein the zirconia sintered body has a transmittance of 40% or more for light of 700 nm wavelength through a thickness of 0.5 mm.

[4] The zirconia sintered body according to any one of [1] to [3], wherein the zirconia sintered body comprises a cubical crystal as a predominant crystal phase.

[5] The zirconia sintered body according to any one of [1] to [4], wherein the zirconia sintered body comprises a monoclinic crystal in a fraction of 5% or less with respect to a tetragonal crystal and a cubical crystal after being immersed in 180° C. hot water for 5 hours.

[6] The zirconia sintered body according to any one of [1] to [5], wherein the zirconia sintered body is a dental material.

[7] The zirconia sintered body according to [6], wherein the zirconia sintered body is a prosthesis for an occlusal surface of a posterior tooth, or a prosthesis for an incisal region of a front tooth.

[8] A zirconia shaped body comprising a fluorescent agent, wherein the zirconia shaped body comprises 4.5 to 9.0 mol % yttria, and has a three-point flexural strength of 500 MPa or more after being sintered at 1,100° C. for 2 hours under ordinary pressure, and a crystal grain size of 180 nm or less after being sintered at 1,100° C. for 2 hours under ordinary pressure.

[9] The zirconia shaped body according to [8], wherein the zirconia shaped body is formed from zirconia particles.

[10] The zirconia shaped body according to [8] or [9], wherein the fluorescent agent comprises a metallic element, and the zirconia shaped body comprises the fluorescent agent in an amount of 0.001 to 1 mass % in terms of an oxide of the metallic element relative to a mass of zirconia.

[11] The zirconia shaped body according to any one of [8] to [10], wherein the zirconia shaped body has a transmittance of 40% or more for light of 700 nm wavelength through a thickness of 0.5 mm after being sintered at 1,100° C. for 2 hours under ordinary pressure.

[12] A zirconia calcined body comprising a fluorescent agent, wherein the zirconia calcined body comprises 4.5 to 9.0 mol % yttria, and has a three-point flexural strength of 500 MPa or more after being sintered at 1,100° C. for 2 hours under ordinary pressure, and a crystal grain size of 180 nm or less after being sintered at 1,100° C. for 2 hours under ordinary pressure.

[13] The zirconia calcined body according to [12], wherein the zirconia calcined body is a product of calcination of a zirconia shaped body formed from zirconia particles.

[14] The zirconia calcined body according to [12] or [13], wherein the fluorescent agent contains a metallic element, and the zirconia calcined body comprises the fluorescent agent in an amount of 0.001 to 1 mass % in terms of an oxide of the metallic element relative to a mass of zirconia.

[15] The zirconia calcined body according to any one of [12] to [14], wherein the zirconia calcined body has a transmittance of 40% or more for light of 700 nm wavelength through a thickness of 0.5 mm after being sintered at 1,100° C. for 2 hours under ordinary pressure.

[16] A method for producing the zirconia shaped body of any one of [8] to [11], comprising a shaping step of shaping zirconia particles, wherein the zirconia particles comprise 4.5 to 9.0 mol % yttria, and have an average primary particle diameter of 20 nm or less.

[17] The method according to [16], wherein the method further comprises a step of mixing a zirconia particle-containing slurry and a liquid-state fluorescent agent.

[18] The method according to [16] or [17], wherein the shaping step is a step of slip casting a slurry comprising zirconia particles and a fluorescent agent.

[19] The method according to [16] or [17], wherein the shaping step is a step of gel casting a slurry comprising zirconia particles and a fluorescent agent.

[20] The method according to [16] or [17], wherein the shaping step is a step of pressing a powder comprising zirconia particles and a fluorescent agent.

[21] The method according to [16] or [17], wherein the shaping step is a step of shaping a composition comprising zirconia particles, a fluorescent agent, and a resin.

[22] The method according to [16] or [17], wherein the shaping step is a step of polymerizing a composition comprising zirconia particles, a fluorescent agent, and a polymerizable monomer.

[23] The method according to [22], wherein the shaping step is a stereolithography process.

[24] A method for producing the zirconia calcined body of any one of [12] to [15], comprising a step of calcining the zirconia shaped body of any one of [8] to [11], or the zirconia shaped body obtained by the method of any one of [16] to [23].

[25] The method according to [24], wherein the calcination is carried out between 300° C. or more and less than 900° C.

[26] A method for producing the zirconia sintered body of any one of [1] to [7], comprising a step of sintering the zirconia shaped body of any one of [8] to [11], or the zirconia shaped body obtained by the method of any one of [16] to [23], under ordinary pressure.

[27] The method according to [26], wherein the sintering is carried out between 900° C. or more and 1,200° C. or less.

[28] A method for producing the zirconia sintered body of any one of [1] to [7], comprising sintering the zirconia calcined body of any one of [12] to [15], or the zirconia calcined body obtained by the method of [24] or [25], under ordinary pressure.

[29] The method according to [28], wherein the sintering is carried out between 900° C. or more and 1,200° C. or less.

Advantageous Effects of Invention

According to the present invention, a zirconia sintered body is provided that excels in both translucency and strength despite containing a fluorescent agent. A zirconia shaped body and a zirconia calcined body are also provided from which such a zirconia sintered body can be obtained. The present invention also provides methods for conveniently producing these.

DESCRIPTION OF EMBODIMENTS

An embodiment of the present invention is described below. It is to be noted that the following descriptions do not limit the present invention.

Zirconia Sintered Body

A zirconia sintered body of the present invention comprises a fluorescent agent. By containing a fluorescent agent, the zirconia sintered body exhibits fluorescence. The type of fluorescent agent is not particularly limited, and the fluorescent agent may be one or more fluorescent agents capable of emitting fluorescence under the light of any wavelength. Examples of such fluorescent agents include those containing metallic elements. Examples of the metallic elements include Ga, Bi, Ce, Nd, Sm, Eu, Gd, Tb, Dy, and Tm. The fluorescent agent may contain one of these metallic elements alone, or may contain two or more of these metallic elements. For advantages such as enhancing the effects of the present invention, the metallic elements are preferably Ga, Bi, Eu, Gd, and Tm, more preferably Bi and Eu. The fluorescent agent used to produce the zirconia sintered body of the present invention may be, for example, an oxide, hydroxide, acetate, or nitrate of the metallic elements above. The fluorescent agent may be, for example, $Y_2SiO_5$:Ce, $Y_2SiO_5$:Tb, $(Y,Gd,Eu)BO_3$, $Y_2O_3$:Eu, YAG:Ce, $ZnGa_2O_4$:Zn, or $BaMgAl_{10}O_{17}$:Eu.

The content of the fluorescent agent in the zirconia sintered body is not particularly limited, and may be appropriately adjusted according to such factors as the type of fluorescent agent, and the use of the zirconia sintered body. However, for advantages such as suitability as dental prostheses, the fluorescent agent content is preferably 0.001 mass % or more, more preferably 0.005 mass % or more, even more preferably 0.01 mass % or more, and is preferably 1 mass % or less, more preferably 0.5 mass % or less, even more preferably 0.1 mass % or less in terms of an oxide of the metallic element contained in the fluorescent agent, relative to the mass of the zirconia contained in the zirconia sintered body. With the fluorescent agent contained in an amount equal to or greater than these lower limits, the zirconia sintered body can produce fluorescence comparable to that of natural human teeth. With the fluorescent agent contained in an amount equal to or less than the foregoing upper limits, decrease of translucency and strength can be reduced.

The zirconia sintered body of the present invention may contain a colorant. By containing a colorant, the zirconia sintered body can have a color. The type of colorant is not particularly limited, and the colorant may be a known pigment commonly used to color ceramics, or a known dental liquid colorant. Examples of the colorant include colorants containing metallic elements, specifically, oxides, composite oxides, and salts containing metallic elements such as iron, vanadium, praseodymium, erbium, chromium, nickel, and manganese. The colorant may be a commercially available colorant, for example, such as the Prettau Colour Liquid manufactured by Zirkonzahn. The zirconia sintered body may contain one kind of colorant, or may contain two or more kinds of colorants.

The content of the colorant in the zirconia sintered body is not particularly limited, and may be appropriately adjusted according to such factors as the type of colorant, and the use of the zirconia sintered body. However, for advantages such as suitability as dental prostheses, the colorant content is preferably 0.001 mass % or more, more preferably 0.005 mass % or more, even more preferably 0.01 mass % or more, and is preferably 5 mass % or less, more preferably 1 mass % or less, even more preferably 0.5 mass % or less, and may be 0.1 mass % or less, or 0.05 mass % or less in terms of an oxide of the metallic element contained in the colorant, relative to the mass of the zirconia contained in the zirconia sintered body.

With the present invention, a zirconia sintered body having excellent translucency can be obtained, despite that the zirconia sintered body contains a fluorescent agent. The zirconia sintered body of the present invention may contain a translucency adjuster for adjustment of translucency in the zirconia sintered body. Specific examples of the translucency adjuster include aluminum oxide, titanium oxide, silicon dioxide, zircon, lithium silicate, and lithium disilicate. The zirconia sintered body may contain one kind of translucency adjuster, or may contain two or more kinds of translucency adjusters.

The content of the translucency adjuster in the zirconia sintered body is not particularly limited, and may be appropriately adjusted according to such factors as the type of translucency adjuster, and the use of the zirconia sintered body. However, for advantages such as suitability as dental prostheses, the content of translucency adjuster is preferably 0.1 mass % or less relative to the mass of the zirconia contained in the zirconia sintered body.

The zirconia sintered body of the present invention contains 4.5 to 9.0 mol % yttria. The zirconia sintered body cannot have sufficient translucency with an yttria content of less than 4.5 mol %. The strength decreases when the yttria content in the zirconia sintered body is more than 9.0 mol %. For advantages such as producing a zirconia sintered body having improved translucency and strength, the yttria content in the zirconia sintered body is preferably 5.0 mol % or more, more preferably 5.5 mol % or more, and is preferably 8.0 mol % or less, more preferably 7.0 mol % or less. It is to be noted that the yttria content in the zirconia sintered body is a fraction (mol %) of the number of moles of yttria with respect to the total number of moles of zirconia and yttria.

The zirconia sintered body of the present invention has a crystal grain size of 180 nm or less. Sufficient translucency cannot be obtained with a crystal grain size of more than 180 nm. For advantages such as producing a zirconia sintered body having improved translucency, the crystal grain size is preferably 140 nm or less, more preferably 120 nm or less, even more preferably 115 nm or less, and may be 110 nm or less. The lower limit of crystal grain size is not particularly limited, and the crystal grain size may be, for example, 50 nm or more, or 100 nm or more. The crystal grain size of the zirconia sintered body can be determined by taking a micrograph of zirconia sintered body cross sections with a field emission scanning electron microscope (FE-SEM), and finding a mean value of diameters of circles corresponding to 10 arbitrarily selected particles from the micrograph (the diameters of true circles having the same areas as these particles).

The zirconia sintered body of the present invention excels in strength, despite containing a fluorescent agent. The zirconia sintered body of the present invention has a three-point flexural strength of 500 MPa or more, preferably 600 MPa or more, more preferably 650 MPa or more, even more preferably 700 MPa or more, particularly preferably 800 MPa or more. With the three-point flexural strength falling in these ranges, the zirconia sintered body of the present invention can have a reduced chance of breaking or fracturing in the mouth when used as, for example, a dental prosthesis. The upper limit of three-point flexural strength is not particularly limited, and the three-point flexural strength may be, for example, 1,500 MPa or less, or 1,000 MPa or less. The three-point flexural strength of zirconia sintered body can be measured in compliance with JIS R 1601:2008.

The zirconia sintered body of the present invention excels in translucency, despite containing a fluorescent agent. The zirconia sintered body of the present invention has a transmittance of preferably 40% or more, more preferably 45% or more, and may have a transmittance of 46% or more, 48% or more, 50% or more, or 52% or more for light of 700 nm wavelength through a thickness of 0.5 mm. With the transmittance falling in these ranges, the zirconia sintered body can more easily satisfy the level of translucency required for the incisal region when used as, for example, a dental prosthesis. The upper limit of transmittance is not particularly limited, and the transmittance may be, for example, 60% or less, or 57% or less. The transmittance of zirconia sintered body for light of 700 nm wavelength through a thickness of 0.5 mm may be measured with a spectrophotometer. For example, the transmittance can be measured with an integrating sphere by measuring light from a light source passing and scattering on a specimen, using a spectrophotometer (Hitachi spectrophotometer, Model U-3900H manufactured by Hitachi High-Technologies Corporation). In the measurement, the transmittance for light of 700 nm wavelength may be determined after measuring transmittance in a wavelength region of 300 to 750 nm. The specimen used for measurement may be a disc-shaped zirconia sintered body having mirror polished surfaces and measuring 15 mm in diameter and 0.5 mm in thickness.

The predominant crystal phase of the zirconia sintered body of the present invention may be a tetragonal crystal or a cubical crystal. However, the predominant crystal phase is preferably a cubical crystal. The zirconia sintered body of the present invention is preferably at least 50% cubical crystal, more preferably at least 70% cubical crystal. The fraction of the cubical crystal in the zirconia sintered body may be determined by crystal phase analysis. Specifically, the fraction of cubical crystal may be determined by X-ray diffraction (XRD) analysis of a mirror finished surface portion of the zirconia sintered body, using the following formula.

$$f_c = 100 \times I_c/(I_m + I_t + I_c)$$

Here, $f_c$ represents the fraction (%) of the cubical crystal in the zirconia sintered body, $I_m$ represents the height of a peak (a peak attributed to the (11-1) plane of a monoclinic crystal) near 2θ=28 degrees, $I_t$ represents the height of a peak (a peak attributed to the (111) plane of a tetragonal crystal) near 2θ=30 degrees, and $I_c$ represents the height of a peak (a peak attributed to the (111) plane of the cubical crystal) near 2θ=30 degrees. When the peak near 2θ=30 degrees appears as a peak attributed to a mixed phase of the (111) plane of the tetragonal crystal and the (111) plane of the cubical crystal, and separation is difficult to achieve for the peak attributed to the (111) plane of the tetragonal crystal and the peak attributed to the (111) plane of the cubical crystal, $I_t$ and $I_c$ can be determined by first determining the ratio of tetragonal crystal and cubical crystal using a technique such as the Rietveld method, and then multiplying the ratio by the height ($I_{t+c}$) of the peak attributed to the mixed phase.

In the zirconia sintered body of the present invention, the fraction of monocinic crystal with respect to tetragonal crystal and cubical crystal after the zirconia sintered body is immersed in 180° C. hot water for 5 hours is preferably 5% or less, more preferably 3% or less, even more preferably 1% or less. With the fraction falling in these ranges, volume changes due to aging can be reduced, and breakage can be prevented when the zirconia sintered body is used as, for example, a dental prosthesis. The fraction can be determined by mirror polishing a surface of the zirconia sintered body, and measuring the mirror polished surface portion by X-ray diffraction (XRD) analysis after the zirconia sintered body is immersed in 180° C. hot water for 5 hours, using the following formula.

$$f_m = 100 \times I_m/(I_{t+c})$$

Here, $f_m$ represents the fraction (%) of the monocinic crystal with respect to the tetragonal crystal and the cubical crystal in the zirconia sintered body immersed in 180° C. hot water for 5 hours, $I_m$ represents the height of a peak (a peak attributed to the (11-1) plane of the monoclinic crystal) near 2θ=28 degrees, and $I_{t+c}$ represents the height of a peak (a peak attributed to a mixed phase of the (111) plane of the tetragonal crystal and the (111) plane of the cubical crystal) near 2θ=30 degrees. When $I_{t+c}$ cannot be easily specified as a result of the peak near 2θ=30 degrees separately appearing as a peak attributed to the (111) plane of the tetragonal crystal and a peak attributed to the (111) plane of the cubical crystal, $I_{t+c}$ can be determined as the sum of the height ($I_t$) of the peak attributed to the (111) plane of the tetragonal crystal and the height ($I_c$) of the peak attributed to the (111) plane of the cubical crystal.

The method of production of the zirconia sintered body of the present invention is not particularly limited, and the zirconia sintered body may be produced by, for example, sintering a fluorescent agent- and 4.5 to 9.0 mol % yttria-containing zirconia shaped body under ordinary pressure. The zirconia sintered body of the present invention also may be produced by calcining such a zirconia shaped body, and sintering the resulting zirconia calcined body containing a fluorescent agent and 4.5 to 9.0 mol % yttria under ordinary pressure. The present invention encompasses a zirconia shaped body containing a fluorescent agent and 4.5 to 9.0 mol % yttria, and that has a three-point flexural strength of 500 MPa or more after being sintered at 1,100° C. for 2 hours under ordinary pressure, and a crystal grain size of 180 nm or less after being sintered at 1,100° C. for 2 hours under ordinary pressure; and a zirconia calcined body containing a fluorescent agent and 4.5 to 9.0 mol % yttria, and that has a three-point flexural strength of 500 MPa or more after being sintered at 1,100° C. for 2 hours under ordinary pressure, and a crystal grain size of 180 nm or less after being sintered at 1,100° C. for 2 hours under ordinary pressure. The zirconia sintered body of the present invention having excellent translucency and excellent strength despite containing a fluorescent agent can be produced with ease from such a zirconia shaped body and zirconia calcined body.

Zirconia Shaped Body

The zirconia shaped body of the present invention comprises a fluorescent agent and 4.5 to 9.0 mol % yttria, and has a three-point flexural strength of 500 MPa or more after being sintered at 1,100° C. for 2 hours under ordinary pressure, and a crystal grain size of 180 nm or less after being sintered at 1,100° C. for 2 hours under ordinary pressure. The zirconia shaped body of the present invention can be formed from zirconia particles.

The fluorescent agent contained in the zirconia shaped body of the present invention may be the same fluorescent agent contained in the zirconia sintered body to be produced. The content of the fluorescent agent in the zirconia shaped body may be appropriately adjusted according to, for example, the content of the fluorescent agent in the zirconia sintered body to be produced. Specifically, the content of the fluorescent agent in the zirconia shaped body is preferably 0.001 mass % or more, more preferably 0.005 mass % or more, even more preferably 0.01 mass % or more, and is preferably 1 mass % or less, more preferably 0.5 mass % or less, even more preferably 0.1 mass % or less in terms of an oxide of the metallic element contained in the fluorescent agent, relative to the mass of the zirconia contained in the zirconia shaped body.

When producing a zirconia sintered body containing a colorant, it is preferable that the colorant be contained in the zirconia shaped body. The content of the colorant in the zirconia shaped body may be appropriately adjusted according to, for example, the content of the colorant in the zirconia sintered body to be produced. Specifically, the content of the colorant in the zirconia shaped body is preferably 0.001 mass % or more, more preferably 0.005 mass % or more, even more preferably 0.01 mass % or more, and is preferably 5 mass % or less, more preferably 1 mass % or less, even more preferably 0.5 mass % or less, and may be 0.1 mass % or less, or 0.05 mass % or less in terms of an oxide of the metallic element contained in the colorant, relative to the mass of the zirconia contained in the zirconia shaped body.

When producing a zirconia sintered body containing a translucency adjuster, it is preferable that the translucency adjuster be contained in the zirconia shaped body. The content of the translucency adjuster in the zirconia shaped body may be appropriately adjusted according to, for example, the content of the translucency adjuster in the zirconia sintered body to be produced. Specifically, the content of the translucency adjuster in the zirconia shaped body is preferably 0.1 mass % or less relative to the mass of the zirconia contained in the zirconia shaped body.

The yttria content in the zirconia shaped body of the present invention may be the same as the yttria content in the zirconia sintered body to be produced. Specifically, the yttria content in the zirconia shaped body is 4.5 mol % or more, preferably 5.0 mol % or more, more preferably 5.5 mol % or more, and is 9.0 mol % or less, preferably 8.0 mol % or less, more preferably 7.0 mol % or less. It is to be noted that the yttria content in the zirconia shaped body is a fraction (mol %) of the number of moles of yttria with respect to the total number of moles of zirconia and yttria.

The density of the zirconia shaped body is not particularly limited, and varies with factors such as the method of production of the zirconia shaped body. However, for advantages such as producing a more compact zirconia sintered body, the density is preferably 3.0 g/cm$^3$ or more, more preferably 3.2 g/cm$^3$ or more, even more preferably 3.4 g/cm$^3$ or more. The upper limit of density is not particularly limited, and may be, for example, 6.0 g/cm$^3$ or less, or 5.8 g/cm$^3$ or less.

The shape of the zirconia shaped body is not particularly limited, and may be chosen as desired according to use. However, for example, considering ease of handing of when producing a zirconia calcined body to be used as a mill blank for producing a dental material such as a dental prosthesis, the zirconia shaped body preferably has a disc or a prism shape (e.g., rectangular). By using a technique such as stereolithography, a shape corresponding to the shape desired for the product zirconia sintered body can be imparted to the zirconia shaped body during its production, as will be described later. The present invention also encompasses zirconia shaped bodies having such desired shapes.

The zirconia shaped body may have a monolayer structure or a multilayer structure. With a multilayered zirconia shaped body, the resulting zirconia sintered body can have a multilayer structure, which allows translucency and other physical properties to be locally altered.

For considerations such as ease of handling, the zirconia shaped body has a biaxial flexural strength in a range of preferably 2 to 10 MPa, more preferably 5 to 8 MPa. The biaxial flexural strength of zirconia shaped body can be measured in compliance with JIS T 6526:2012.

The zirconia shaped body of the present invention has a crystal grain size of 180 nm or less after being sintered at 1,100° C. for 2 hours under ordinary pressure (after the zirconia shaped body is formed into a zirconia sintered body; the sintering performed under these conditions may be preceded by calcination at 700° C. for 2 hours under ordinary pressure). In this way, the zirconia sintered body of the present invention having excellent translucency can be produced with ease. For advantages such as producing a zirconia sintered body having even higher translucency, the crystal grain size is preferably 140 nm or less, more preferably 120 nm or less, even more preferably 115 nm or less, and may be 110 nm or less. The lower limit of crystal grain size is not particularly limited, and the crystal grain size may be, for example, 50 nm or more, or 100 nm or more. Here, the crystal grain size is a measured value obtained in the same manner as in the crystal grain size measurement described above in conjunction with the zirconia sintered body.

The zirconia shaped body of the present invention has a three-point flexural strength of 500 MPa or more after being sintered at 1,100° C. for 2 hours under ordinary pressure (after the zirconia shaped body is formed into a zirconia sintered body; the sintering performed under these conditions may be preceded by calcination at 700° C. for 2 hours under ordinary pressure). In this way, the zirconia sintered body of the present invention having excellent strength can be produced with ease. For advantages such as producing a zirconia sintered body having even higher strength, the three-point flexural strength is preferably 600 MPa or more, more preferably 650 MPa or more, even more preferably 700 MPa or more, particularly preferably 800 MPa or more. The upper limit of three-point flexural strength is not particularly limited, and the three-point flexural strength may be, for example, 1,500 MPa or less, or 1,000 MPa or less. Here, the three-point flexural strength is a measured value obtained in the same manner as in the three-point flexural strength measurement described above in conjunction with the zirconia sintered body.

The zirconia shaped body has a transmittance of preferably 40% or more for light of 700 nm wavelength through a thickness of 0.5 mm after being sintered at 1,100° C. for 2 hours under ordinary pressure (after the zirconia shaped body is formed into a zirconia sintered body; the sintering performed under these conditions may be preceded by calcination at 700° C. for 2 hours under ordinary pressure). In this way, the zirconia sintered body of the present invention having excellent transparency can be produced with ease. For advantages such as producing a zirconia sintered body having even higher translucency, the transmittance is more preferably 45% or more, and may be 46% or more, 48% or more, 50% or more, or 52% or more. The upper limit of transmittance is not particularly limited, and the transmittance may be, for example, 60% or less, or 57% or less. Here, the transmittance is a measured value obtained in the same manner as in the measurement of transmittance for light of 700 nm wavelength through a thickness of 0.5 mm described above in conjunction with the zirconia sintered body.

Method of Production of Zirconia Shaped Body

The method of production of the zirconia shaped body of the present invention is not particularly limited. However, for easy production of the zirconia sintered body of the present invention that excels in both translucency and strength, it is preferable that the zirconia shaped body be produced by a method that includes a shaping step of shaping zirconia particles, more preferably a method that includes a shaping step of shaping zirconia particles in the presence of a fluorescent agent.

The yttria content in the zirconia particles used is preferably the same as the yttria content in the zirconia shaped body, and, in turn, the yttria content in the zirconia calcined body and the zirconia sintered body to be produced. Specifically, the yttria content in the zirconia particles is preferably 4.5 mol % or more, more preferably 5.0 mol % or more, even more preferably 5.5 mol % or more, and is preferably 9.0 mol % or less, more preferably 8.0 mol % or less, even more preferably 7.0 mol % or less. It is to be noted that the yttria content in the zirconia particles is a fraction (mol %) of the number of moles of yttria with respect to the total number of moles of zirconia and yttria.

The zirconia particles used have an average primary particle diameter of preferably 30 nm or less. In this way, the zirconia shaped body of the present invention, and, in turn, the zirconia calcined body and the zirconia sintered body of the present invention can be obtained with ease. For considerations such as ease of production of the zirconia shaped body of the present invention, and, in turn, the zirconia calcined body and the zirconia sintered body of the present invention, the average primary particle diameter of the zirconia particles is more preferably 20 nm or less, even more preferably 15 nm or less, and may be 10 nm or less, and is preferably 1 nm or more, more preferably 5 nm or more. The average primary particle diameter of zirconia particles can be determined by, for example, taking a micrograph of zirconia particles (primary particles) with a transmission electron microscope (TEM), and finding a mean value of particle diameters (maximum diameters) measured for arbitrarily chosen 100 particles from the photographed image.

For considerations such as ease of production of the zirconia shaped body of the present invention, and, in turn, the zirconia calcined body and the zirconia sintered body of the present invention, it is preferable that the zirconia particles contain primary particles of 50 nm or more in an amount of preferably 5 mass % or less, more preferably 3 mass % or less, even more preferably 1 mass % or less. The content can be measured by using, for example, a zeta potential meter.

The method of preparation of zirconia particles is not particularly limited, and the zirconia particles may be prepared by using, for example, a breakdown process that pulverizes coarse particles into a fine powder, or a building-up process that synthesizes particles through nucleation and nuclear growth from atoms and ions. The building-up process is more preferred for obtaining high-purity, fine zirconia particles.

The breakdown process may use, for example, a ball mill or bead mill for pulverization. Here, it is preferable to use microsize pulverization media, for example, pulverization media of 100 m or less. Preferably, the pulverization is followed by classification.

The building-up process may be, for example, vapor-phase pyrolysis, which is a process by which an oxoacid salt of high-vapor-pressure metal ions, or a high-vapor-pressure organometallic compound is decomposed under heat through vaporization to precipitate an oxide; vapor-phase reaction, which synthesizes particles through vapor-phase chemical reaction of a high-vapor-pressure metallic compound gas with a reactive gas; evaporative concentration, in which a feedstock material is heated to evaporate, and cooled rapidly in an inert gas of a predetermined pressure to condense the steam into a fine particle form; a melt process that forms a powder by cooling and solidifying small liquid droplets of melt; solvent evaporation, which causes precipitation in a supersaturated state created by increasing the concentration by evaporating the solvent in a solution; or a precipitation process in which the solute concentration is brought to a supersaturated state through reaction with a precipitating agent or hydrolysis, and a poorly soluble compound such as an oxide and hydroxide is precipitated through nucleation and nuclear growth.

The precipitation process can be sub-divided into processes that include: homogenous precipitation in which a precipitating agent is generated in a solution by chemical reaction to eliminate local heterogeneity in the concentration of precipitating agent; coprecipitation in which a plurality of metal ions coexisting in a solution is simultaneously precipitated by addition of a precipitating agent; a hydrolysis process that produces an oxide or hydroxide through hydrolysis from a metal salt solution, an alcohol solution of metal alkoxide or the like; and solvothermal synthesis that produces an oxide or hydroxide from a high-temperature high-pressure fluid. The solvothermal synthesis is further divided into processes that include hydrothermal synthesis that uses water as solvent, and supercritical synthesis that uses a supercritical fluid such as water or carbon dioxide as solvent.

Regardless of the building-up process, it is preferable to increase the precipitation rate to obtain finer zirconia particles. Preferably, the zirconia particles produced are classified.

The zirconium source in the building-up process may be, for example, nitrate, acetate, chloride, or alkoxide. Specifically, for example, zirconium oxychloride, zirconium acetate, and zirconyl nitrate may be used.

In order to achieve the foregoing yttria content ranges in the zirconia particles, yttria may be added in the process of producing zirconia particles. For example, a solid solution of yttria may be formed in zirconia particles. The yttrium source may be, for example, nitrate, acetate, chloride, or alkoxide. Specifically, for example, yttrium chloride, yttrium acetate, and yttrium nitrate may be used.

As required, the zirconia particles may be subjected to a surface treatment in advance with a known surface treatment agent selected from, for example, organic compounds having acidic groups; fatty acid amides such as saturated fatty acid amides, unsaturated fatty acid amides, saturated fatty acid bisamides, and unsaturated fatty acid bisamides; and organometallic compounds such as silane coupling agents (organosilicon compounds), organic titanium compounds, organic zirconium compounds, and organic aluminum compounds. A surface treatment of zirconia particles allows for adjustments of miscibility with a liquid having a surface tension at 25° C. of 50 mN/m or less when such a liquid is contained in the dispersion medium of a slurry used when preparing a zirconia particle- and fluorescent agent-containing powder, as will be described later. A surface treatment also allows the zirconia particles to have adjusted miscibility with a polymerizable monomer, for example, when producing the zirconia shaped body using a method that includes polymerizing a composition containing zirconia particles, a fluorescent agent, and a polymerizable monomer, as will be described later. The surface treatment agent is preferably an organic compound having an acidic group because of advantages such as desirable miscibility with a liquid having a surface tension at 25° C. of 50 mN/m or less, and the ability to increase the strength of the resulting zirconia shaped body by improving the chemical bonding between the zirconia particles and a polymerizable monomer.

Examples of the organic compounds having acidic groups include organic compounds having at least one acidic group, such as a phosphoric acid group, a carboxylic acid group, a pyrophosphoric acid group, a thiophosphoric acid group, a phosphonic acid group, and a sulfonic acid group. Preferred are phosphoric acid group-containing organic compounds having at least one phosphoric acid group, and carboxylic acid group-containing organic compounds having at least one carboxylic acid group, of which the phosphoric acid group-containing organic compounds are more preferred. The zirconia particles may be subjected to a surface treatment with one type of surface treatment agent, or with two or more types of surface treatment agents. In the case where the zirconia particles are subjected to a surface treatment with two or more types of surface treatment agents, the surface treatment layer produced may be a surface treatment layer of a mixture of two or more surface treatment agents, or a surface treatment layer of a multilayer structure of a plurality of surface treatment layers.

Examples of the phosphoric acid group-containing organic compounds include 2-ethylhexyl acid phosphate, stearyl acid phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, and ammonium salts thereof.

Examples of the carboxylic acid group-containing organic compounds include succinic acid, oxalic acid, octanoic acid, decanoic acid, stearic acid, polyacrylic acid, 4-methyloctanoic acid, neodecanoic acid, pivalic acid, 2,2-dimethylbutyric acid, 3,3-dimethylbutyric acid, 2,2-dimethylvaleric acid, 2,2-diethylbutyric acid, 3,3-diethylbutyric acid, naphthenic acid, cyclohexane dicarboxylic acid, (meth)acrylic acid, N-(meth)acryloylglycine, N-(meth)acryloylaspartic acid, O-(meth)acryloyltyrosine, N-(meth)acryloyltyrosine, N-(meth)acryloyl-p-aminobenzoic acid, N-(meth)acryloyl-o-aminobenzoic acid, p-vinyl benzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate, 2-(meth)acryloyloxyethyl hydrogen maleate, 2-(2-(2-methoxyethoxy)ethoxy) acetic acid (commonly known as "MEEAA"), 2-(2-methoxyethoxy)acetic acid (commonly known as "MEAA"), succinic acid mono[2-(2-methoxyethoxy)ethyl] ester, maleic acid mono[2-(2-methoxyethoxy)ethyl]ester, glutaric acid mono[2-(2-methoxyethoxy)ethyl]ester, malonic acid, glutaric acid, 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxybutyl trimellitate, 4-(meth)acryloyloxyhexyl trimellitate, 4-(meth)acryloyloxydecyl trimellitate, 2-(meth)acryloyloxyethyl-3'-(meth)acryloyloxy-2'-(3,4-dicarboxybenzoyloxy)propylsuccinate, and acid anhydrides, acid halides, alkali metal salts, and ammonium salts thereof.

It is also possible to use organic compounds having at least one acidic group different from the acidic groups mentioned above (e.g., a pyrophosphoric acid group, a thiophosphoric acid group, a phosphonic acid group, and a sulfonic acid group). For example, the organic compounds mentioned in WO2012/042911 may be used as such organic compounds.

Examples of the saturated fatty acid amides include palmitamide, stearamide, and behenamide. Examples of the unsaturated fatty acid amides include oleamide and erucamide. Examples of the saturated fatty acid bisamides include ethylene-bis-palmitamide, ethylene-bis-stearamide, and hexamethylene-bis-stearamide. Examples of the unsaturated fatty acid bisamides include ethylene-bis-oleamide, hexamethylene-bis-oleamide, and N,N'-dioleyl sebacamide.

Examples of the silane coupling agents (organosilicon compounds) include compounds represented by $R^1{}_n SiX_{4-n}$ (wherein $R^1$ is a substituted or unsubstituted hydrocarbon group of 1 to 12 carbon atoms, X is an alkoxy group of 1 to 4 carbon atoms, a hydroxyl group, a halogen atom, or a hydrogen atom, and n is an integer of 0 to 3, and $R^1$ and X each may be the same or different when a plurality of $R^1$ and X exists).

Specific examples of the silane coupling agents (organosilicon compounds) include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyltris(β-methoxyethoxy)silane, 3,3,3-trifluoropropyltrimethoxysilane, methyl-3,3,3-trifluoropropyldimethoxysilane, β-(3,4-epoxycyclohexyl) ethyltrimethoxysilane, γ-glycidoxypropyltrimethoxysilane, γ-glycidoxypropylmethyldiethoxysilane, γ-glycidoxypropyltriethoxysilane, γ-methacryloyloxypropylmethyldimethoxysilane, γ-methacryloyloxypropylmethyldiethoxysilane, N-(β-aminoethyl) γ-aminopropylmethyldimethoxysilane, N-(β-aminoethyl) γ-aminopropyltrimethoxysilane, N-(β-aminoethyl) γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloyloxyalkyltrimethoxysilane [3 to 12 carbon atoms between the (meth)acryloyloxy group and the silicon atom, for example, such as in γ-methacryloyloxypropyltrimethoxysilane], and ω-(meth)acryloyloxyalkyltriethoxysilane [3 to 12 carbon atoms between the (meth)acryloyloxy group and the silicon atom, for example, such as in γ-methacryloyloxypropyltriethoxysilane]. As used herein, the notation "(meth)acryloyl" is meant to be inclusive of both methacryloyl and acryloyl.

Among these examples, silane coupling agents having functional groups are preferred. Particularly preferred are ω-(meth)acryloyloxyalkyltrimethoxysilane [3 to 12 carbon atoms between the (meth)acryloyloxy group and the silicon atom], ω-(meth)acryloyloxyalkyltriethoxysilane [3 to 12 carbon atoms between the (meth)acryloyloxy group and the silicon atom], vinyltrimethoxysilane, vinyltriethoxysilane, vinyltriacetoxysilane, and γ-glycidoxypropyltrimethoxysilane.

Examples of the organic titanium compounds include tetramethyl titanate, tetraisopropyl titanate, tetra-n-butyl titanate, butyl titanate dimers, and tetra(2-ethylhexyl)titanate.

Examples of the organic zirconium compounds include zirconium isopropoxide, zirconium n-butoxide, zirconium acetylacetonate, zirconyl acetate.

Examples of the organic aluminum compounds include aluminum acetylacetonate, and aluminum organic acid salt chelate compounds.

The surface treatment method is not particularly limited, and may be a known method, for example, such as a method the adds the surface treatment agent by spraying it while vigorously stirring the zirconia particles, or a method that disperses or dissolves the zirconia particles and the surface treatment agent in a suitable solvent, and removes the solvent. The solvent may be a dispersion medium containing a liquid having a surface tension at 25° C. of 50 mN/m or less, as will be described later. The zirconia particles and the surface treatment agent may be subjected to a reflux or a high-temperature high-pressure process (e.g., autoclaving) after being dispersed or dissolved.

In producing a zirconia shaped body using the method having a shaping step of shaping zirconia particles, the shaping step is not particularly limited. However, for advantages such as ease of production of the zirconia shaped body of the present invention, and, in turn, the zirconia calcined body and the zirconia sintered body of the present invention, the shaping step is preferably any one of the following steps:

(i) a step of slip casting a slurry containing zirconia particles and a fluorescent agent;
(ii) a step of gel casting a slurry containing zirconia particles and a fluorescent agent;
(iii) a step of pressing a powder containing zirconia particles and a fluorescent agent;
(iv) a step of shaping a composition containing zirconia particles, a fluorescent agent, and a resin; and
(v) a step of polymerizing a composition containing zirconia particles, a fluorescent agent, and a polymerizable monomer.

Slurry Containing Zirconia Particles and Fluorescent Agent

The method of preparation of a slurry containing zirconia particles and a fluorescent agent is not particularly limited, and the slurry may be obtained by, for example, mixing a zirconia particle-containing slurry with a fluorescent agent. The zirconia particle-containing slurry may be one obtained after the breakdown or building-up process described above, or may be a commercially available product.

Preferably, a slurry containing zirconia particles and a fluorescent agent is prepared by mixing a zirconia particle-containing slurry with a liquid-state fluorescent agent because it enables the zirconia shaped body and the zirconia calcined body of the present invention to be easily obtained by preventing mixing of coarse particles, and thereby allows for easy production of the zirconia sintered body of the present invention that excels in both translucency and strength despite containing a fluorescent agent. The liquid-state fluorescent agent may be, for example, a solution or a dispersion of a fluorescent agent, preferably a solution of a fluorescent agent. The solution is not particularly limited, and may be, for example, an aqueous solution. The aqueous solution may be, for example, a dilute nitric acid solution or a dilute hydrochloric acid solution, and may be appropriately selected according to conditions such as the type of the fluorescent agent used.

When producing a zirconia shaped body containing a colorant and/or a translucency adjuster, and, in turn, a zirconia calcined body and a zirconia sintered body containing a colorant and/or a translucency adjuster, the colorant and/or translucency adjuster may be added to the slurry containing zirconia particles and a fluorescent agent. In this case, it is preferable that the colorant and/or translucency adjuster be mixed into the zirconia particle-containing slurry in a liquid form such as a solution or a dispersion.

Powder Containing Zirconia Particles and Fluorescent Agent

The method of preparation of a powder containing zirconia particles and a fluorescent agent is not particularly limited, and the powder may be produced by dry blending powdery zirconia particles with a powdery fluorescent agent (here, a colorant and/or a translucency adjuster also may be dry blended when adding a colorant and/or a translucency adjuster to the zirconia shaped body, and, in turn, to the zirconia calcined body and the zirconia sintered body). However, for advantages such as enabling production of a more homogenous zirconia sintered body of improved physical properties, it is preferable that the powder be obtained by drying the slurry containing zirconia particles and a fluorescent agent. The slurry subjected to drying may additionally contain a colorant and/or a translucency adjuster.

The drying method is not particularly limited, and may be, for example, spray drying, supercritical drying, freeze drying, hot-air drying, and drying under reduced pressure. For advantages such as inhibiting particle aggregation during the drying process and obtaining a more compact zirconia sintered body, it is preferable to use any of spray drying, supercritical drying, and freeze drying, more preferably spray drying or supercritical drying, even more preferably spray drying.

The zirconia particle- and fluorescent agent-containing slurry to be dried may be a slurry containing water as dispersion medium. However, for advantages such as inhibiting particle aggregation during the drying process and obtaining a more compact zirconia sintered body, the slurry is preferably a slurry containing a dispersion medium other than water, for example, such as an organic solvent.

Examples of the organic solvent include alcohols such as methanol, ethanol, 1-propanol, 2-propanol, 1-butanol, 2-butanol, tert-butyl alcohol, 2-methoxyethanol, 2-ethoxyethanol, 2-(2-ethoxyethoxy)ethanol, diethylene glycol monobutyl ether, and glycerin; ketones such as acetone, and methyl ethyl ketone; ethers such as tetrahydrofuran, diethyl ether, diisopropyl ether, and 1,4-dioxane, and dimethoxyethane (including modified ethers such as propylene glycol monomethyl ether acetate (commonly known as "PGMEA"), preferably ether-modified ethers and/or ester-modified ethers, more preferably ether-modified alkylene glycols and/or ester-modified alkylene glycols); esters such as ethyl acetate and butyl acetate; hydrocarbons such as hexane and toluene; and halogenated hydrocarbons such as chloroform and carbon tetrachloride. These organic solvents may be used alone, or two or more thereof may be used in combination. Considering safety against the body and ease of removal, the organic solvent is preferably a water-soluble organic solvent. Specifically, the organic solvent is more preferably ethanol, 2-propanol, tert-butyl alcohol, 2-ethoxyethanol, 2-(2-ethoxyethoxy)ethanol, propylene glycol monomethyl ether acetate, acetone, or tetrahydrofuran.

When using spray drying in particular, it is preferable that the dispersion medium in the zirconia particle- and fluorescent agent-containing slurry to be dried contain a liquid having a surface tension at 25° C. of 50 mN/m or less because it enables a more compact zirconia sintered body to be obtained by inhibiting particle aggregation during the drying process. From this viewpoint, the surface tension of the liquid is preferably 40 mN/m or less, more preferably 30 mN/m or less.

The surface tension at 25° C. may be a value from, for example, the Handbook of Chemistry and Physics. For liquids that are not included in this reference, the values recited in WO2014/126034 are usable. The surface tensions at 25° C. of liquids that are not included in either of these documents may be determined by using a known measurement method, for example, such as the ring method or the Wilhelmy method. Preferably, the surface tension at 25° C. is measured using the automatic surface tensiometer CBVP-Z manufactured by Kyowa Interface Science Co., Ltd., or the SIGMA702 manufactured by KSV Instruments Ltd.

The liquid may be an organic solvent having the foregoing ranges of surface tension. The organic solvent may be any of the organic solvents exemplified above and having the foregoing ranges of surface tension. However, for advantages such as inhibiting particle aggregation during the drying process and obtaining a more compact zirconia sintered body, the organic solvent is preferably at least one selected from the group consisting of methanol, ethanol, 2-methoxyethanol, 1,4-dioxane, 2-ethoxyethanol, and 2-(2-ethoxyethoxy)ethanol, more preferably at least one selected from the group consisting of methanol, ethanol, 2-ethoxyethanol, and 2-(2-ethoxyethoxy)ethanol.

For advantages such as inhibiting particle aggregation during the drying process and obtaining a more compact zirconia sintered body, the content of the liquid in the dispersion medium is preferably 50 mass % or more, more preferably 80 mass % or more, even more preferably 95 mass % or more, particularly preferably 99 mass % or more.

A slurry containing a dispersion medium other than water can be obtained by replacing the dispersion medium in a slurry containing water as dispersion medium. The method used to replace the dispersion medium is not particularly limited. For example, a method may be used that removes water after adding a dispersion medium other than water (e.g., an organic solvent) to a slurry containing water as dispersion medium. In removing water, part or all of the dispersion medium other than water may be removed with water. The process of adding a dispersion medium other than water and the subsequent removal of water may be repeated multiple times. Alternatively, a method may be used that precipitates the dispersoid after adding a dispersion medium other than water to a slurry containing water as dispersion medium. It is also possible to replace the dispersion medium with a specific organic solvent in a slurry containing water as dispersion medium, followed by further replacement with another organic solvent.

The fluorescent agent may be added after the replacement of dispersion medium. However, for advantages such as obtaining a more homogenous zirconia sintered body of improved physical properties, the fluorescent agent is added preferably before the replacement of dispersion medium. Similarly, for advantages such as obtaining a more homogenous zirconia sintered body of improved physical properties, it is preferable to add a colorant and/or a translucency adjuster before the replacement of dispersion medium when adding a colorant and/or a translucency adjuster to the slurry, though these may be added after the dispersion medium is replaced.

The zirconia particle- and fluorescent agent-containing slurry to be dried may be subjected to a dispersion process that involves heat and pressure, for example, such as a reflux process or a hydrothermal treatment. The zirconia particle- and fluorescent agent-containing slurry to be dried may be subjected to a mechanical dispersion process using, for example, a roller mill, a colloid mill, a high-pressure spray disperser, an ultrasonic disperser, a vibration mill, a planetary mill, or a bead mill. The slurry may be subjected to one of these processes, or two or more of these processes.

The zirconia particle- and fluorescent agent-containing slurry to be dried may contain one or more other components, for example, such as a binder, a plasticizer, a dispersant, an emulsifier, an antifoaming agent, a pH adjuster, and a lubricant. By containing such other components (particularly, for example, a binder, a dispersant, and an antifoaming agent), it may be possible to inhibit particle aggregation during the drying process, and obtain a more compact zirconia sintered body.

Examples of the binder include polyvinyl alcohol, methylcellulose, carboxymethylcellulose, acrylic binders, wax binders, polyvinyl butyral, polymethylmethacrylate, and ethylcellulose.

Examples of the plasticizer include polyethylene glycol, glycerin, propylene glycol, and dibutyl phthalic acid.

Examples of the dispersant include ammonium polycarboxylates (e.g., triammonium citrate), ammonium polyacrylates, acryl copolymer resins, acrylic acid ester copolymers, polyacrylic acids, bentonite, carboxymethylcellulose, anionic surfactants (for example, polyoxyethylene alkyl ether phosphate esters such as polyoxyethylene lauryl ether phosphate ester), non-ionic surfactants, oleic glycerides, amine surfactants, and oligosugar alcohols.

Examples of the emulsifier include alkyl ethers, phenyl ether, sorbitan derivatives, and ammonium salts.

Examples of the antifoaming agent include alcohols, polyethers, polyethylene glycol, silicone, and waxes.

Examples of the pH adjuster include ammonia, ammonium salts (including ammonium hydroxides such as tetramethylammonium hydroxide), alkali metal salts, and alkali-earth metal salts.

Examples of the lubricant include polyoxyethylene alkylate ether, and waxes.

For advantages such as inhibiting particle aggregation during the drying process and obtaining a more compact zirconia sintered body, the moisture content in the zirconia particle- and fluorescent agent-containing slurry to be dried is preferably 3 mass % or less, more preferably 1 mass % or less, even more preferably 0.1 mass % or less. The moisture content may be measured with a Karl Fisher moisture content meter.

The drying conditions in the foregoing drying methods are not particularly limited, and may be appropriately selected from known drying conditions. When using an organic solvent as dispersion medium, it is preferable that drying be carried out in the presence of a nonflammable gas, more preferably in the presence of nitrogen, in order to reduce the risk of explosion during the drying process.

In the case of supercritical drying, the supercritical fluid is not particularly limited, and may be, for example, water or carbon dioxide. However, for advantages such as inhibiting particle aggregation and obtaining a more compact zirconia sintered body, the supercritical fluid is preferably carbon dioxide.

Composition Containing Zirconia Particles, Fluorescent Agent, and Resin

The method of preparation of a composition containing zirconia particles, a fluorescent agent, and a resin is not particularly limited, and the composition may be obtained by, for example, mixing the zirconia particle- and fluorescent agent-containing powder with a resin.

Composition Containing Zirconia Particles, Fluorescent Agent and Polymerizable Monomer The method of preparation of a composition containing zirconia particles, a fluorescent agent, and a polymerizable monomer is not particularly limited, and the composition may be obtained by, for example, mixing the zirconia particle- and fluorescent agent-containing powder with a polymerizable monomer.

(i) Slip Casting

In producing a zirconia shaped body by the method that includes a step of slip casting a slurry containing zirconia particles and a fluorescent agent, the slip casting method is not particularly limited, and may be, for example, a method in which a slurry containing zirconia particles and a fluorescent agent is dried after being poured into a mold.

For advantages such as ease of pouring into a mold, and increasing the usable lifetime of a mold by preventing long drying times, the content of the dispersion medium in the zirconia particle- and fluorescent agent-containing slurry used is preferably 80 mass % or less, more preferably 50 mass % or less, even more preferably 20 mass % or less.

The slurry may be poured into a mold under ordinary pressure. However, it is preferable for production efficiency that the slurry be poured into a mold under increased pressure conditions. The type of the mold used for slip casting is not particularly limited, and the mold may be, for example, a porous mold made of plaster, resin, ceramic, or the like. Resin molds and ceramic molds are desirable in terms of durability.

The zirconia particle- and fluorescent agent-containing slurry used for slip casting may additionally contain at least one of a colorant and a translucency adjuster such as above, and may additionally contain one or more other components, for example, such as the binders, plasticizers, dispersants, emulsifiers, antifoaming agents, pH adjusters, and lubricants exemplified above.

(ii) Gel Casting

In producing a zirconia shaped body by the method that includes a step of gel casting a slurry containing zirconia particles and a fluorescent agent, the gel casting method is not particularly limited, and may be, for example, a method in which a zirconia particle- and fluorescent agent-containing slurry is shaped into a wet body by a process such as gelation, followed by drying.

For advantages such as preventing long drying times and inhibiting cracking during drying, the content of the dispersion medium in the zirconia particle- and fluorescent agent-containing slurry used is preferably 80 mass % or less, more preferably 50 mass % or less, even more preferably 20 mass % or less.

The gelation may be initiated by addition of, for example, a gelatinizer, or may be achieved by adding and polymerizing a polymerizable monomer. The type of the mold used is not particularly limited, and the mold may be, for example, a porous mold made of plaster, resin, ceramic, or the like, or a nonporous mold made of metal, resin, or the like.

The type of gelatinizer is not particularly limited, and, for example, a water-soluble gelatinizer may be used Specifically, for example, agarose or gelatin may preferably be used. The gelatinizer may be one kind of gelatinizer used alone, or may be two or more kinds of gelatinizers used in combination. For considerations such as inhibiting cracking during sintering, the gelatinizer content is preferably 10 mass % or less, more preferably 5 mass % or less, even more preferably 1 mass % or less relative to the mass of the slurry after the gelatinizer is added.

The type of polymerizable monomer is not particularly limited. Examples of the polymerizable monomer include 2-hydroxyethyl(meth)acrylate, 3-hydroxypropyl(meth)acrylate, 4-hydroxybutyl(meth)acrylate, 6-hydroxyhexyl(meth) acrylate, 10-hydroxydecyl(meth)acrylate, propylene glycol mono(meth)acrylate, glycerol mono(meth)acrylate, erythritol mono(meth)acrylate, N-methylol(meth)acrylamide, N-hydroxyethyl(meth)acrylamide, and N,N-(dihydroxyethyl)(meth)acrylamide. The polymerizable monomer may be used alone, or two or more thereof may be used in combination.

For considerations such as inhibiting cracking during sintering, the content of the polymerizable monomer is preferably 10 mass % or less, more preferably 5 mass % or less, even more preferably 1 mass % or less relative to the mass of the slurry after the polymerizable monomer is added.

When gelation is achieved by polymerization of the polymerizable monomer, the polymerization is carried out preferably with use of a polymerization initiator. The type of polymerization initiator is not particularly limited. However, the polymerization initiator is particularly preferably a photopolymerization initiator. The photopolymerization initiator may be appropriately selected from photopolymerization initiators commonly used in industry, preferably from photopolymerization initiators used in dentistry.

Specific examples of the photopolymerization initiator include (bis)acylphosphine oxides (including salts), thioxanthones (including salts such as quaternary ammonium salts), ketals, α-diketones, coumarins, anthraquinones, benzoinalkyl ether compounds, and α-aminoketone compounds. The photopolymerization initiator may be used alone, or two or more thereof may be used in combination. Among these, the photopolymerization initiator is preferably at least one selected from the group consisting of (bis)acylphosphine oxides and α-diketones. In this way, polymerization (gelation) can be achieved both in the ultraviolet region (including the near-ultraviolet region) and in the visible light region. Specifically, polymerization (gelation) can sufficiently proceed regardless of whether the light source is a laser such as an Ar laser or a He—Cd laser; or a light such as a halogen lamp, a xenon lamp, a metal halide lamp, a light emitting diode (LED), a mercury lamp, and a fluorescent lamp.

Examples of the acylphosphine oxides in the (bis)a-cylphosphine oxides include 2,4,6-trimethylbenzoyldiphe-nylphosphine oxide (commonly known as "TPO"), 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di-(2, 6-dimethylphenyl)phosphonate, sodium salts of 2,4,6-trimethylbenzoylphenylphosphine oxide, potassium salts of 2,4,6-trimethylbenzoyldiphenylphosphine oxide, and ammonium salts of 2,4,6-trimethylbenzoyldiphenylphosphine oxide.

Examples of the bisacylphosphine oxides in the (bis) acylphosphine oxides include bis(2,6-dichlorobenzoyl)phe-nylphosphine oxide, bis(2,6-dichlorobenzoyl)-2,5-dimeth-ylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl) phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis (2,3,6-trimethylbenzoyl)-2,4,4-trimethylpentylphosphine oxide. It is also possible to use other compounds, including, for example, the compounds mentioned in JP-A-2000-159621.

Preferred among these (bis)acylphosphine oxides are 2,4, 6-trimethylbenzoyldiphenylphosphine oxide, 2,4,6-trimeth-ylbenzoylmethoxyphenylphosphine oxide, bis(2,4,6-trim-ethylbenzoyl)phenylphosphine oxide, and sodium salts of 2,4,6-trimethylbenzoylphenylphosphine oxide.

Examples of the o-diketones include diacetyl, benzyl, camphorquinone, 2,3-pentadione, 2,3-octadione, 9,10-phenanthrenequinone, 4,4'-oxybenzyl, and acenaphthene-quinone. Preferred is camphorquinone, particularly when using a light source of the visible light region.

The zirconia particle- and fluorescent agent-containing slurry used for gel casting may additionally contain at least one of a colorant and a translucency adjuster such as above, and may additionally contain one or more other components, such as the binders, plasticizers, dispersants, emulsifiers, antifoaming agents, pH adjusters, and lubricants exemplified above, as with the case of the slurry used for slip casting.

The method of drying the shaped wet body is not particularly limited, and may be, for example, natural drying, hot-air drying, vacuum drying, dielectric heating, induction heating, or constant-temperature constant-humidity drying. The drying may be achieved by using one of these methods, or two or more of these methods. For advantages such as inhibiting cracking during drying, the preferred drying methods are natural drying, dielectric heating, induction heating, and constant-temperature constant-humidity drying.

(iii) Pressing

In producing a zirconia shaped body by the method that includes a step of pressing a powder containing zirconia particles and a fluorescent agent, the pressing is not particularly limited to specific methods, and may be achieved by using a known pressing machine. Specific examples of the pressing method include uniaxial pressing. In order to increase the density of the zirconia shaped body produced, it is preferable that uniaxial pressing be followed by cold isostatic pressing (CIP).

The zirconia particle- and fluorescent agent-containing powder used for pressing may additionally contain at least one of a colorant and a translucency adjuster such as above, and may additionally contain one or more other components, such as the binders, plasticizers, dispersants, emulsifiers, antifoaming agents, pH adjusters, and lubricants exemplified above. These components may be added at the time of preparing the powder.

(iv) Shaping of Resin-Containing Composition

In producing a zirconia shaped body by the method that includes a step of shaping a composition containing zirconia particles, a fluorescent agent, and a resin, the composition shaping method is not limited to specific methods, and the composition may be shaped by using a method, for example, such as injection molding, cast molding, and extrusion molding. It is also possible to shape the composition using a lamination shaping technique (e.g., 3D printing), for example, such as fused deposition modeling (FDM), an inkjet method, or a powder-binder lamination technique. Preferred as the shaping method are injection molding and cast molding, more preferably injection molding.

The resin is not limited to particular types of resins, and resins that function as binders may preferably be used. Specific examples of the resin include fatty acids such as paraffin wax, polyvinyl alcohol, polyethylene, a polypropylene, ethylene-vinyl acetate copolymer, polystyrene, atactic polypropylene, (meth)acrylic resin, and stearic acid. These resins may be used alone, or two or more thereof may be used in combination.

The composition containing zirconia particles, a fluorescent agent, and a resin may additionally contain at least one of a colorant and a translucency adjuster such as above, and may additionally contain one or more other components, such as the plasticizers, dispersants, emulsifiers, antifoaming agents, pH adjusters, and lubricants exemplified above.

(v) Polymerization of Composition Containing Polymerizable Monomer

Polymerization of the composition containing zirconia particles, a fluorescent agent, and a polymerizable monomer can polymerize the polymerizable monomer in the composition, and cure the composition. In producing a zirconia shaped body by the method that includes a polymerization step, the method is not particularly limited to specific methods, and may be, for example, (a) a method that polymerizes the zirconia particle-, fluorescent agent-, and polymerizable monomer-containing composition in a mold; or (b) stereolithography (SLA) using the composition containing zirconia particles, a fluorescent agent, and a polymerizable monomer. Of these, (b) stereolithography is preferred. By stereolithography, a shape corresponding to the shape desired for the product zirconia sintered body can be imparted to the zirconia shaped body at the time of its production. This makes the stereolithography a potentially preferred method, particularly when the zirconia sintered body of the present invention is used as a dental material such as a dental prosthesis.

The type of the polymerizable monomer in the zirconia particle-, fluorescent agent-, and polymerizable monomer-containing composition is not particularly limited, and the polymerizable monomer may be one selected from monofunctional polymerizable monomers such as monofunctional (meth)acrylates, and monofunctional (meth)acrylamides, and polyfunctional polymerizable monomers such as bifunctional aromatic compounds, bifunctional aliphatic compounds, and tri and higher functional compounds. The polymerizable monomer may be used alone, or two or more thereof may be used in combination. Among these, polyfunctional polymerizable monomers are preferred, particularly when stereolithography is used.

Examples of the monofunctional (meth)acrylates include (meth)acrylates having hydroxyl groups, such as 2-hydroxyethyl(meth)acrylate, 2-hydroxypropyl(meth)acrylate, 3-hydroxypropyl(meth)acrylate, 4-hydroxybutyl(meth)acrylate, 6-hydroxyhexyl(meth)acrylate, 10-hydroxydecyl(meth) acrylate, propylene glycol mono(meth)acrylate, glycerol mono(meth)acrylate, and erythritol mono(meth)acrylate; alkyl(meth)acrylates such as methyl(meth)acrylate, ethyl (meth)acrylate, propyl(meth)acrylate, isopropyl(meth)acrylate, n-butyl(meth)acrylate, sec-butyl(meth)acrylate, t-butyl (meth)acrylate, isobutyl(meth)acrylate, n-hexyl(meth) acrylate, lauryl(meth)acrylate, cetyl(meth)acrylate, and stearyl(meth)acrylate; alicyclic(meth)acrylates, such as cyclohexyl(meth)acrylate, and isobornyl(meth)acrylate; aromatic group-containing(meth)acrylates, such as benzyl (meth)acrylate, and phenyl(meth)acrylate; and (meth)acrylates having functional groups, such as 2,3-dibromopropyl (meth)acrylate, 3-(meth)acryloyloxypropyltrimethoxysilane, and 11-(meth)acryloyloxyundecyltrimethoxysilane.

Examples of the monofunctional (meth)acrylamides include (meth)acrylamide, N-(meth)acryloylmorpholine, N,N-dimethyl(meth)acrylamide, N,N-diethyl(meth)acrylamide, N,N-di-n-propyl(meth)acrylamide, N,N-di-n-butyl (meth)acrylamide, N,N-di-n-hexyl(meth)acrylamide, N,N-di-n-octyl(meth)acrylamide, N,N-di-2-ethylhexyl(meth) acrylamide, N-hydroxyethyl(meth)acrylamide, and N,N-di (hydroxyethyl)(meth)acrylamide.

Among these monofunctional polymerizable monomers, (meth)acrylamides are preferred, and N-(meth)acryloylmorpholine, N,N-dimethyl(meth)acrylamide, and N,N-diethyl (meth)acrylamide are more preferred for their desirable polymerizability.

Examples of the bifunctional aromatic compounds include 2,2-bis((meth)acryloyloxyphenyl)propane, 2,2-bis [4-(3-acryloyloxy-2-hydroxyprop oxy)phenyl]propane, 2,2-bis[4-(3-methacryloyloxy-2-hydroxypropoxy)phenyl]propane (commonly known as "Bis-GMA"), 2,2-bis(4-(meth) acryloyloxyethoxyphenyl)propane, 2,2-bis(4-(meth) acryloyloxypolyethoxyphenyl)propane, 2,2-bis(4-(meth) acryloyloxydiethoxyphenyl)propane, 2,2-bis(4-(meth) acryloyloxytetraethoxyphenyl)propane, 2,2-bis(4-(meth) acryloyloxypentaethoxyphenyl)propane, 2,2-bis(4-(meth) acryloyloxydipropoxyphenyl)propane, 2-(4-(meth) acryloyloxydiethoxyphenyl)-2-(4-(meth) acryloyloxyethoxyphenyl)propane, 2-(4-(meth) acryloyloxydiethoxyphenyl)-2-(4-(meth) acryloyloxyditriethoxyphenyl)propane, 2-(4-(meth) acryloyloxydipropoxyphenyl)-2-(4-(meth) acryloyloxytriethoxyphenyl)proane, 2,2-bis(4-(meth) acryloyloxypropoxyphenyl)propane, 2,2-bis(4-(meth) acryloyloxyisopropoxyphenyl)propane, and 1,4-bis(2-(meth)acryloyloxyethyl)pyromellitate. Among these, 2,2-bis [4-(3-methacryloyloxy-2-hydroxypropoxy)phenyl]propane (commonly known as "Bis-GMA"), and 2,2-bis(4-(meth) acryloyloxypolyethoxyphenyl)propane are preferred for their desirable polymerizability and ability to provide desirable strength for the zirconia shaped body produced. Preferred as 2,2-bis(4-(meth)acryloyloxypolyethoxyphenyl) propane is 2,2-bis(4-methacryloyloxypolyethoxyphenyl) propane (a compound with an average number of moles of ethoxy group added of 2.6; commonly known as "D-2.6E").

Examples of the bifunctional aliphatic compounds include glycerol di(meth)acrylate, ethylene glycol di(meth) acrylate, diethylene glycol di(meth)acrylate, triethylene glycol di(meth)acrylate, propylene glycol di(meth)acrylate, butylene glycol di(meth)acrylate, neopentyl glycol di(meth) acrylate, polyethylene glycol di(meth)acrylate, 1,3-butanediol di(meth)acrylate, 1,4-butanediol di(meth)acrylate, 1,6-hexanediol di(meth)acrylate, 2-ethyl-1,6-hexanediol di(meth)acrylate, 1,9-nonanediol di(meth)acrylate, 1,10-decanediol di(meth)acrylate, 1,2-bis(3-methacryloyloxy-2-hydroxypropoxy)ethane, and 2,2,4-trimethylhexamethylene bis(2-carbamoyloxyethyl)dimethacrylate (commonly known as "UDMA"). Among these, triethylene glycol dimethacrylate (commonly known as "TEGDMA"), and 2,2,4-trimethylhexamethylene bis(2-carbamoyloxyethyl)dimethacrylate are preferred for their desirable polymerizability and ability to provide desirable strength for the zirconia shaped body produced.

Examples of the tri and higher functional compounds include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy)propane-1,3-diol]tetra(meth)acrylate, and 1,7-diacryloyloxy-2,2,6,6-tetra(meth)acryloyloxymethyl-4-oxyheptane. Among these, N,N-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane are preferred for their desirable polymerizability and ability to provide desirable strength for the zirconia shaped body produced.

Regardless of whether the method (a) or (b) is used, it is preferable that a polymerization initiator be used for the polymerization of the composition, and that the composition contain a polymerization initiator. The type of polymerization initiator is not particularly limited, and the polymerization initiator is particularly preferably a photopolymerization initiator. The photopolymerization initiator may be appropriately selected from photopolymerization initiators commonly used in industry, preferably from photopolymerization initiators used in dentistry. Specific examples of the photopolymerization initiator include those exemplified above in conjunction with gel casting, and are omitted to avoid redundancy.

The composition containing zirconia particles, a fluorescent agent, and a polymerizable monomer may additionally contain at least one of a colorant and a translucency adjuster such as above, and may additionally contain one or more other components, such as the plasticizers, dispersants, emulsifiers, antifoaming agents, pH adjusters, and lubricants exemplified above.

In producing a zirconia shaped body by stereolithography using the composition containing zirconia particles, a fluorescent agent, and a polymerizable monomer, the stereolithography is not particularly limited to specific methods, and may be achieved by appropriately using a known method. For example, the desired zirconia shaped body may be obtained by forming layers of desired shapes layer-by-layer through photo-polymerization of a liquid composition with, for example, ultraviolet light or a laser, using a stereolithography device.

In obtaining the zirconia shaped body by stereolithography, the content of the zirconia particles in the zirconia particle-, fluorescent agent-, and polymerizable monomer-containing composition should preferably be as high as possible from the viewpoint of sinterability in a later step. Specifically, the zirconia particle content is preferably 20 mass % or more, more preferably 30 mass % or more, even more preferably 40 mass % or more, particularly preferably 50 mass % or more. From the principle of layer formation in stereolithography, it is preferable that the composition have a viscosity that falls in a certain range. To this end, the content of the zirconia particles in the composition is preferably 90 mass % or less, more preferably 80 mass % or less, even more preferably 70 mass % or less, particularly preferably 60 mass % or less. Adjustment of composition viscosity may be of particular importance when stereolithography is performed using the constrained surface method, in which light is applied upward through the bottom of a container to form a zirconia shaped body layer-by-layer, and when the composition needs to be smoothly flown in between the bottom surface of the previously cured layer and the bottom of the container for the formation of the next layer after the cured layer is elevated upward by the height of one layer.

Specifically, the composition has a viscosity of preferably 20,000 mPa·s or less, more preferably 10,000 mPa·s or less, even more preferably 5,000 mPa·s or less, and is preferably 100 mPa·s or more, in terms of a viscosity at 25° C. Because the viscosity of the composition tends to increase with increase of the zirconia particle content, it is preferable to appropriately adjust the balance between zirconia particle content and viscosity in the composition in a way suited for the performance and other characteristics of the stereolithography device, taking into consideration factors such as the balance between the rate of the stereolithography process and the accuracy of the zirconia shaped body produced. The viscosity may be measured with an E-type viscometer.

Zirconia Calcined Body

The zirconia calcined body of the present invention comprises a fluorescent agent, and 4.5 to 9.0 mol % yttria, and has a three-point flexural strength of 500 MPa or more after being sintered at 1,100° C. for 2 hours under ordinary pressure, and a crystal grain size of 180 nm or less after being sintered at 1,100° C. for 2 hours under ordinary pressure. The zirconia calcined body of the present invention may be a product obtained after the calcination of the zirconia shaped body formed from zirconia particles.

The fluorescent agent contained in the zirconia calcined body of the present invention may be the same fluorescent agent contained in the zirconia sintered body to be produced. The content of the fluorescent agent in the zirconia calcined body may be appropriately adjusted according to, for example, the content of the fluorescent agent in the zirconia sintered body to be produced. Specifically, the content of the fluorescent agent contained in the zirconia calcined body is preferably 0.001 mass % or more, more preferably 0.005 mass % or more, even more preferably 0.01 mass % or more, and is preferably 1 mass % or less, more preferably 0.5 mass % or less, even more preferably 0.1 mass % or less in terms of an oxide of the metallic element contained in the fluorescent agent, relative to the mass of the zirconia contained in the zirconia calcined body.

When producing a zirconia sintered body containing a colorant, it is preferable that the colorant be contained in the zirconia calcined body. The colorant content in the zirconia calcined body may be appropriately adjusted according to, for example, the content of the colorant in the zirconia sintered body to be produced. Specifically, the colorant content in the zirconia calcined body is preferably 0.001 mass % or more, more preferably 0.005 mass % or more, even more preferably 0.01 mass % or more, and is preferably 5 mass % or less, more preferably 1 mass % or less, even more preferably 0.5 mass % or less, and may be 0.1 mass % or less, or 0.05 mass % or less in terms of an oxide of the metallic element contained in the colorant, relative to the mass of the zirconia contained in the zirconia calcined body.

When producing a zirconia sintered body containing a translucency adjuster, it is preferable that the translucency adjuster be contained in the zirconia calcined body. The content of the translucency adjuster in the zirconia calcined body may be appropriately adjusted according to, for example, the content of the translucency adjuster in the zirconia sintered body to be produced. Specifically, the content of the translucency adjuster contained in the zirconia calcined body is preferably 0.1 mass % or less relative to the mass of the zirconia contained in the zirconia calcined body.

The yttria content in the zirconia calcined body of the present invention may be the same as that in the zirconia sintered body to be produced. Specifically, the yttria content in the zirconia calcined body is 4.5 mol % or more, preferably 5.0 mol % or more, more preferably 5.5 mol % or more, and is 9.0 mol % or less, preferably 8.0 mol % or less, more preferably 7.0 mol % or less. It is to be noted that the yttria content in the zirconia calcined body is a fraction (mol %) of the number of moles of yttria with respect to the total number of moles of zirconia and yttria.

The density of the zirconia calcined body is not particularly limited, and preferably falls in a range of 3.0 to 6.0 g/m$^3$, more preferably 3.2 to 5.8 g/m$^3$, though the density varies with conditions such as the method of production of the zirconia shaped body used for the production of the zirconia calcined body.

The shape of the zirconia calcined body is not particularly limited, and may be chosen as desired according to use. However, for example, considering ease of handing of when using the zirconia calcined body as a mill blank for producing a dental material such as a dental prosthesis, the zirconia calcined body preferably has a disc or a prism shape (e.g., rectangular). The zirconia calcined body may be cut (milled) into the desired shape according to use before being formed into a zirconia sintered body, as will be described later. However, the present invention also encompasses zirconia calcined bodies of desired shapes imparted after cutting (milling). The zirconia calcined body may have a monolayer structure or a multilayer structure. However, with a multilayered zirconia calcined body, the resulting zirconia sintered body can have a multilayer structure, which allows translucency and other physical properties to be locally altered.

For advantages such as maintaining the shape of the work in the process of working using a cutting machine, and improving the ease of cutting itself, the three-point flexural strength of the zirconia calcined body preferably falls in a range of 10 to 70 MPa, more preferably 20 to 60 MPa. The three-point flexural strength of the zirconia calcined body may be a measured value obtained from a 5 mm×40 mm×10 mm test piece using a multi-purpose tester at a span length of 30 mm and a crosshead speed of 0.5 mm/min.

The zirconia calcined body of the present invention has a crystal grain size of 180 nm or less after being sintered at 1,100° C. for 2 hours under ordinary pressure (after being formed into a zirconia sintered body). In this way, the zirconia sintered body of the present invention having excellent translucency can be produced with ease. For advantages such as obtaining a zirconia sintered body having even higher translucency, the crystal grain size is preferably 140 nm or less, more preferably 120 nm or less, even more preferably 115 nm or less, and may be 110 nm or less. The lower limit of crystal grain size is not particularly limited, and the crystal grain size may be, for example, 50 nm or more, or 100 nm or more. The crystal grain size can be measured in the same manner as in the crystal grain size measurement described above in conjunction with the zirconia sintered body.

The zirconia calcined body of the present invention has a three-point flexural strength of 500 MPa or more after being sintered at 1,100° C. for 2 hours under ordinary pressure (after being formed into a zirconia sintered body). In this way, the zirconia sintered body of the present invention having excellent strength can be produced with ease. For advantages such as obtaining a zirconia sintered body having even higher strength, the three-point flexural strength is preferably 600 MPa or more, more preferably 650 MPa or more, even more preferably 700 MPa or more, particularly preferably 800 MPa or more. The upper limit of three-point flexural strength is not particularly limited, and the three-point flexural strength may be, for example, 1,500 MPa or less, or 1,000 MPa or less. The three-point flexural strength can be measured in the same manner as in the measurement of three-point flexural strength described above in conjunction with the zirconia sintered body.

The zirconia calcined body has a transmittance of preferably 40% or more for light of 700 nm wavelength through a thickness of 0.5 mm after being sintered at 1,100° C. for 2 hours under ordinary pressure (after being formed into a zirconia sintered body). In this way, the zirconia sintered body of the present invention having excellent translucency can be produced with ease. For advantages such as obtaining a zirconia sintered body having even higher translucency, the transmittance is more preferably 45% or more, and may be 46% or more, 48% or more, 50% or more, or 52% or more. The upper limit of transmittance is not particularly limited, and the transmittance may be, for example, 60% or less, or 57% or less. The transmittance can be measured in the same manner as in the measurement of transmittance for light of 700 nm wavelength through a thickness of 0.5 mm described above in conjunction with the zirconia sintered body.

Method of Production of Zirconia Calcined Body

The zirconia calcined body of the present invention can be obtained by calcining the zirconia shaped body. For advantages such as ease of obtaining the desired zirconia calcined body, the calcination temperature is preferably 300° C. or more, more preferably 400° C. or more, even more preferably 500° C. or more, and is preferably less than 900° C., more preferably 850° C. or less, even more preferably 800° C. or less. With a calcination temperature equal to or greater than the foregoing lower limits, it is possible to effectively inhibit generation of organic material residues. With a calcination temperature equal to or less than the foregoing upper limits, it is possible to reduce the difficulty in cutting (milling) with a cutting machine occurring when the sintering overly proceeds.

The rate of temperature increase in calcination is not particularly limited, and is preferably 0.1° C./min or more, more preferably 0.2° C./min or more, even more preferably 0.5° C./min or more, and is preferably 50° C./min or less, more preferably 30° C./min or less, even more preferably 20° C./min or less. The productivity improves when the rate of temperature increase is equal to or greater than the foregoing lower limits. With a rate of temperature increase equal to or less than the foregoing upper limits, it is possible to reduce the volume difference between inner and outer portions of the zirconia shaped body and the zirconia calcined body, and to reduce cracking and breakage by inhibiting the organic materials from undergoing rapid decomposition when the zirconia shaped body is containing organic materials.

The calcination time in the calcination of the zirconia shaped body is not particularly limited. However, for advantages such as efficiently and stably obtaining the desired zirconia calcined body with good productivity, the calcination time is preferably 0.5 hours or more, more preferably 1 hour or more, even more preferably 2 hours or more, and is preferably 10 hours or less, more preferably 8 hours or less, even more preferably 6 hours or less.

Calcination may be carried out using a calcination furnace. The type of calcination furnace is not particularly limited, and the calcination furnace may be, for example, an electric furnace or a debinding furnace commonly used in industry.

The zirconia calcined body may be cut (milled) into the desired shape according to use, before being formed into a zirconia sintered body. To describe more specifically, the zirconia sintered body of the present invention excels in both translucency and strength despite containing a fluorescent agent, and is particularly preferred as, for example, a dental material such as a dental prosthesis. To this end, the zirconia calcined body may be cut (milled) into a shape corresponding to the shape of such a material so that a zirconia sintered body for use in such applications can be obtained. Cutting (milling) is not limited to specific methods, and may be achieved by using, for example, a known milling device.

Method of Production of Zirconia Sintered Body

As described above, the zirconia sintered body of the present invention can be produced by sintering a zirconia shaped body containing a fluorescent agent and 4.5 to 9.0 mol % yttria, under ordinary pressure. The zirconia sintered body of the present invention also can be produced by sintering a zirconia calcined body containing a fluorescent agent and 4.5 to 9.0 mol % yttria under ordinary pressure.

For advantages such as ease of obtaining the desired zirconia sintered body, the sintering temperature is preferably 900° C. or more, more preferably 1,000° C. or more, even more preferably 1,050° C. or more, and is preferably 1,200° C. or less, more preferably 1,150° C. or less, even more preferably 1,120° C. or less, regardless of whether the zirconia shaped body or the zirconia calcined body is sintered. With a sintering temperature equal to or greater than the foregoing lower limits, sintering can sufficiently proceed, and a compact sintered body can be obtained with ease. With a sintering temperature equal to or less than the foregoing upper limits, it is possible to easily obtain a zirconia sintered body having a crystal grain size within the ranges of the present invention, and to inhibit deactivation of fluorescent agent.

In sintering the zirconia shaped body and the zirconia calcined body, the sintering time is not particularly limited; however, for advantages such as efficiently and stably obtaining the desired zirconia sintered body with good productivity, the sintering time is preferably 5 minutes or more, more preferably 15 minutes or more, even more preferably 30 minutes or more, and is preferably 6 hours or less, more preferably 4 hours or less, even more preferably 2 hours or less, regardless of whether the zirconia shaped body or the zirconia calcined body is sintered.

Sintering may be carried out using a sintering furnace. The type of sintering furnace is not particularly limited, and the sintering furnace may be, for example, an electric furnace or a debinding furnace commonly used in industry. Specifically, when the zirconia sintered body is to be used for dental material applications, it is possible to use a dental porcelain furnace, which operates in a relatively low sintering temperature range, other than using a traditional dental sintering furnace for zirconia.

The zirconia sintered body of the present invention can be produced with ease without hot isostatic pressing (HIP). However, further improvement of translucency and strength can be achieved when the sintering under ordinary pressure is followed by hot isostatic pressing (HIP).

Use of Zirconia Sintered Body

The zirconia sintered body of the present invention is not limited to particular applications. However, because the zirconia sintered body of the present invention excels in both translucency and strength despite containing a fluorescent agent, the zirconia sintered body of the present invention is particularly preferred as a dental material such as a dental prosthesis, and is highly useful not only as a dental prosthesis for the cervical region of a tooth, but as a dental prosthesis for the occlusal surface of a posterior tooth, and the incisal region of a front tooth. The zirconia sintered body of the present invention is particularly preferred for use as a dental prosthesis for the incisal region of a front tooth.

EXAMPLES

The following describes the present invention in greater detail using Examples and Comparative Examples. It is to be noted, however, that the present invention is not limited by the following descriptions. The methods used to measure physical properties are as follows.

(1) Average Primary Particle Diameter of Zirconia Particles

The average primary particle diameter of zirconia particles was determined by taking a micrograph of zirconia particles with a transmission electron microscope (TEM), and finding a mean value of particle diameters (maximum diameters) measured for arbitrarily chosen 100 particles from the photographed image.

(2) Crystal Grain Size

The crystal grain size of zirconia sintered body was determined by taking a micrograph of zirconia sintered body cross sections with a field emission scanning electron microscope (FE-SEM), and finding a mean value of diameters of circles corresponding to 10 arbitrarily selected particles from the micrograph (the diameters of true circles having the same areas as these particles).

(3) Three-Point Flexural Strength

The three-point flexural strength of zirconia sintered body was measured in compliance with JIS R 1601:2008.

(4) Light Transmittance (700 nm Wavelength, 0.5 mm Thickness)

The transmittance of zirconia sintered body for light of 700 nm wavelength through a thickness of 0.5 mm was measured with an integrating sphere by measuring light from a light source passing and scattering on a specimen, using a spectrophotometer (Hitachi spectrophotometer, Model U-3900H manufactured by Hitachi High-Technologies Corporation). In the measurement, the transmittance for light of 700 nm wavelength was determined after measuring transmittance in a wavelength region of 300 to 750 nm. For the measurement, a disc-shaped zirconia sintered body having mirror polished surfaces and measuring 15 mm in diameter and 0.5 mm in thickness was used as a specimen.

(5) Fraction of Cubical Crystal

The fraction of the cubical crystal in zirconia sintered body was determined by crystal phase analysis. Specifically, the fraction of cubical crystal was determined by X-ray diffraction (XRD) analysis of a mirror finished surface portion of the zirconia sintered body, using the following formula.

$$f_c = 100 \times I_c / (I_m + I_t + I_c)$$

Here, $f_c$ represents the fraction (%) of the cubical crystal in zirconia sintered body, $I_m$ represents the height of a peak (a peak attributed to the (11-1) plane of a monocinic crystal) near 2θ=28 degrees, $I_t$ represents the height of a peak (a peak attributed to the (111) plane of a tetragonal crystal) near 2θ=30 degrees, and $I_c$ represents the height of a peak (a peak attributed to the (111) plane of the cubical crystal) near 2θ=30 degrees.

(6) Fraction of Monoclinic Crystal after Hot-Water Treatment

The fraction of monoclinic crystal with respect to tetragonal crystal and cubical crystal after the zirconia sintered body is immersed in 180° C. hot water for 5 hours was determined by mirror polishing a surface of the zirconia sintered body, and measuring the mirror polished surface portion by X-ray diffraction (XRD) analysis after the zirconia sintered body was immersed in 180° C. hot water for 5 hours, using the following formula.

$$f_m = 100 \times I_m / (I_{t+c})$$

Here, $f_m$ represents the fraction (%) of the monocinic crystal with respect to the tetragonal crystal and the cubical crystal in the zirconia sintered body immersed in 180° C. hot water for 5 hours, $I_m$ represents the height of a peak (a peak attributed to the (11-1) plane of the monoclinic crystal) near 2θ=28 degrees, and $I_t+c$ represents the height of a peak (a peak attributed to the mixed phase of the (111) plane of the tetragonal crystal and the (111) plane of the cubical crystal) near 2θ=30 degrees.

(7) Appearance of Zirconia Sintered Body

The appearance (color) of zirconia sintered body was evaluated by visual inspection.

(8) Fluorescence of Zirconia Sintered Body

For evaluation of the fluorescence of zirconia sintered body, the presence or absence of fluorescence under UV light was determined by visual inspection.

Example 1

A molding slurry containing zirconia particles and a fluorescent agent was prepared by adding a dilute nitric acid solution of bismuth nitrate to a water-based zirconia slurry containing 5 mol % yttria (MELox Nanosize 5Y manufactured by MEL Chemicals; average primary particle diameter of zirconia particles=13 nm, zirconia concentration=23 mass %) so that the resulting mixture had a concentration of 0.02 mass % in terms of an oxide of bismuth ($Bi_2O_3$) relative to the mass of zirconia.

The mixture was poured into a plaster mold, and allowed to stand for 2 weeks at room temperature to obtain a zirconia shaped body. The plaster mold was prepared by mixing water into a plaster (Noritake Dental Plaster manufactured by Kuraray Noritake Dental Inc.) in a proportion of 50 mass %. The zirconia shaped body was calcined at 700° C. for 2 hours under ordinary pressure to obtain a zirconia calcined body. The zirconia calcined body was then sintered at 1,100° C. for 2 hours under ordinary pressure to obtain a zirconia sintered body. The zirconia sintered body obtained was white in color, and had fluorescence. The measurement results are presented in Table 1.

The zirconia calcined body produced in the manner described above was cut into shapes of crowns for maxillary central incisor and mandibular first molar using a milling device (Katana H-18 manufactured by Kuraray Noritake Dental Inc.). These were then sintered at 1,100° C. for 2 hours under ordinary pressure to obtain crown-shaped dental prostheses having fluorescence.

Example 2

A 1.0-L mixed aqueous solution of 0.62 mol/L zirconium oxychloride and 0.066 mol/L yttrium chloride, and 0.5 L of a 1.9 mol/L aqueous solution of sodium hydroxide were separately prepared.

After pouring 1.0 L of purified water into a precipitation vessel, the mixed aqueous solution and the sodium hydroxide aqueous solution were simultaneously poured into the vessel to obtain a slurry through coprecipitation of zirconium oxychloride and yttrium chloride. The slurry was filtered and washed, and purified water was added to obtain a 1.0-L slurry having a solid content of 5.0 mass % (a concentration of zirconia and yttria). After adding 22.2 g of acetic acid to the slurry, a hydrothermal treatment was conducted at 200° C. for 3 hours to obtain a zirconia slurry. The zirconia particles contained in the zirconia slurry had an average primary particle diameter of 17 nm.

A molding slurry, a zirconia shaped body, a zirconia calcined body, and a zirconia sintered body were obtained in the same manner as in Example 1, except that the zirconia slurry prepared above was used. The zirconia sintered body obtained was white in color, and had fluorescence. The measurement results are presented in Table 1.

A zirconia calcined body produced in the same manner as described above was cut into shapes of crowns for maxillary central incisor and mandibular first molar using a milling device (Katana H-18 manufactured by Kuraray Noritake Dental Inc.). These were then sintered at 1,100° C. for 2 hours under ordinary pressure to obtain crown-shaped dental prostheses having fluorescence.

Example 3

A zirconia slurry was obtained in the same manner as in Example 2, except that a mixed aqueous solution of 0.62 mol/L zirconium oxychloride and 0.072 mol/L yttrium chloride was used in place of the mixed aqueous solution used in Example 2. The zirconia particles contained in the zirconia slurry had an average primary particle diameter of 17 nm.

A molding slurry, a zirconia shaped body, a zirconia calcined body, and a zirconia sintered body were obtained in the same manner as in Example 1, except that the zirconia slurry prepared above was used. The zirconia sintered body obtained was white in color, and had fluorescence. The measurement results are presented in Table 1.

Example 4

A zirconia slurry was obtained in the same manner as in Example 2, except that a mixed aqueous solution of 0.62 mol/L zirconium oxychloride and 0.093 mol/L yttrium chloride was used in place of the mixed aqueous solution used in Example 2. The zirconia particles contained in the zirconia slurry had an average primary particle diameter of 18 nm.

A molding slurry, a zirconia shaped body, a zirconia calcined body, and a zirconia sintered body were obtained in the same manner as in Example 1, except that the zirconia slurry prepared above was used. The zirconia sintered body obtained was white in color, and had fluorescence. The measurement results are presented in Table 1.

Example 5

A molding slurry, a zirconia shaped body, a zirconia calcined body, and a zirconia sintered body were obtained in the same manner as in Example 1, except that a water-based zirconia slurry containing 8 mol % yttria (MELox Nanosize 8Y manufactured by MEL Chemicals; average primary particle diameter of zirconia particles=13 nm, zirconia concentration=23 mass %) was used in place of the zirconia slurry used in Example 1. The zirconia sintered body obtained was white in color, and had fluorescence. The measurement results are presented in Table 1.

Comparative Example 1

A zirconia shaped body, a zirconia calcined body, and a zirconia sintered body were obtained in the same manner as in Example 1, except that a water-based zirconia slurry containing 5 mol % yttria (MELox Nanosize 5Y manufactured by MEL Chemicals; average primary particle diameter of zirconia particles=13 nm, zirconia concentration=23 mass %) was directly used as a molding slurry. The zirconia sintered body obtained was white in color, but did not have fluorescence. The measurement results are presented in Table 1.

Comparative Example 2

A zirconia slurry was obtained in the same manner as in Example 2, except that a mixed aqueous solution of 0.62 mol/L zirconium oxychloride and 0.130 mol/L yttrium chloride was used in place of the mixed aqueous solution used in Example 2. The zirconia particles contained in the zirconia slurry had an average primary particle diameter of 18 nm.

A zirconia shaped body, a zirconia calcined body, and a zirconia sintered body were obtained in the same manner as in Example 1, except that this zirconia slurry was directly used as a molding slurry. The zirconia sintered body obtained was white in color, but did not have fluorescence. The measurement results are presented in Table 1.

Comparative Example 3

By uniaxial pressing, a zirconia particle powder TZ-8YS (manufactured by Tosoh Corporation; average primary particle diameter=300 nm) was formed into a plate shape measuring 80 mm×40 mm×10 mm in size, and a disc shape measuring 15 mm in diameter and 1.5 mm in thickness. These were subjected to cold isostatic pressing (CIP; 170 MPa pressure) to obtain zirconia shaped bodies of increased density. These zirconia shaped bodies were calcined at 700° C. for 2 hours under ordinary pressure to obtain zirconia calcined bodies. The zirconia calcined bodies were sintered at 1,500° C. for 2 hours under ordinary pressure to obtain zirconia sintered bodies. The zirconia sintered bodies were white in color, but did not have fluorescence. The measurement results are presented in Table 1.

Comparative Example 4

A powder of bismuth nitrate was added to a water-based zirconia slurry containing 5 mol % yttria (MELox Nanosize 5Y manufactured by MEL Chemicals; average primary particle diameter of zirconia particles=13 nm, zirconia concentration=23 mass %) so that the resulting mixture had a concentration of 0.02 mass % in terms of an oxide of bismuth ($Bi_2O_3$) relative to the mass of zirconia. The mixture was then pulverized with a mortar to obtain a molding slurry containing zirconia particles and a fluorescent agent.

A zirconia shaped body, a zirconia calcined body, and a zirconia sintered body were obtained in the same manner as in Example 1, except that the slurry prepared above was used as a molding slurry. The zirconia sintered body was white in color, and had fluorescence. The measurement results are presented in Table 1.

TABLE 1

| Zirconia sintered body | | Example | | | | | Comparative Example | | | |
|---|---|---|---|---|---|---|---|---|---|---|
| | | 1 | 2 | 3 | 4 | 5 | 1 | 2 | 3 | 4 |
| Content of fluorescent agent (*1) | Mass % | 0.02 | 0.02 | 0.02 | 0.02 | 0.02 | — | — | — | 0.02 |
| Content of colorant (*1) | Mass % | — | — | — | — | — | — | — | — | — |
| Content of yttria (*2) | Mol % | 5 | 5 | 5.5 | 7 | 8 | 5 | 9.5 | 8 | 5 |
| Crystal grain size | nm | 108 | 119 | 118 | 119 | 112 | 107 | 112 | 608 | — |
| Three-point flexural strength | MPa | 823 | 662 | 658 | 642 | 650 | 838 | 480 | 350 | 488 |
| Light transmittance (wavelength 700 nm, thickness 0.5 mm) | % | 50 | 46 | 48 | 54 | 55 | 52 | 58 | 32 | 42 |
| Fraction of cubical crystal | % | 100 | 100 | 100 | 100 | 100 | 100 | 100 | 100 | 100 |
| Fraction of monoclinic crystal after hot-water treatment | % | 0 | 0 | 0 | 0 | 0 | 0 | 0 | 0 | 0 |

(*1) Content relative to the mass of zirconia (the content is in terms of an oxide of metallic element)
(*2) Fraction of number of moles of yttria with respect to total number of moles of zirconia and yttria Example 6

An aqueous solution of nickel(II) nitrate was added to a water-based zirconia slurry containing 5 mol % yttria (MELox Nanosize 5Y manufactured by MEL Chemicals; average primary particle diameter of zirconia particles=13 nm, zirconia concentration=23 mass %) so that the resulting mixture had a concentration of 0.02 mass % in terms of an oxide of nickel(II) (NiO) relative to the mass of zirconia. A dilute nitric acid solution of bismuth nitrate was then added to the mixture so that the resulting mixture had a concentration of 0.02 mass % in terms of an oxide of bismuth ($Bi_2O_3$) relative to the mass of zirconia. This produced a molding slurry containing zirconia particles, a fluorescent agent, and a colorant. A zirconia shaped body, a zirconia calcined body, and a zirconia sintered body were obtained in the same manner as in Example 1, except that the slurry prepared above was used as a molding slurry. The zirconia sintered body obtained was red in color, and had fluorescence. The measurement results are presented in Table 2.

Example 7

A dilute nitric acid solution of bismuth nitrate was added to a water-based zirconia slurry containing 5 mol % yttria (MELox Nanosize 5Y manufactured by MEL Chemicals; average primary particle diameter of zirconia particles=13 nm, zirconia concentration=23 mass %) so that the resulting mixture had a concentration of 0.02 mass % in terms of an oxide of bismuth ($Bi_2O_3$) relative to the mass of zirconia. This was followed by addition of tetramethylammonium hydroxide as a pH adjuster, and triammonium citrate as a dispersant. Thereafter, agarose was added as a gelatinizer while stirring the mixture under heat to obtain a molding slurry containing zirconia particles, a fluorescent agent, a pH adjuster, a dispersant, and a gelatinizer.

The molding slurry was poured into a polypropylene mold, and dried at room temperature for 16 days to obtain a zirconia shaped body. The zirconia shaped body was calcined at 700° C. for 2 hours under ordinary pressure to obtain a zirconia calcined body. The zirconia calcined body was then sintered at 1,100° C. for 2 hours under ordinary pressure to obtain a zirconia sintered body. The zirconia sintered body obtained was white in color, and had fluorescence. The measurement results are presented in Table 2.

Example 8

A dilute nitric acid solution of bismuth nitrate was added to 100 parts by mass of a water-based zirconia slurry containing 5 mol % yttria (MELox Nanosize 5Y manufactured by MEL Chemicals; average primary particle diameter of zirconia particles=13 nm, zirconia concentration=23 mass %) so that the resulting mixture had a concentration of 0.02 mass % in terms of an oxide of bismuth ($Bi_2O_3$) relative to the mass of zirconia. This was followed by a dispersion medium replacement procedure, in which 50 parts by mass of 2-ethoxyethanol was added, and concentrated to make the total amount 100 parts by mass, using a rotary evaporator. The dispersion medium replacement procedure was repeated 4 times to obtain a 2-ethoxyethanol-replaced slurry. The 2-ethoxyethanol-replaced slurry had a residual moisture content of 0.05 mass % as measured with a Karl Fisher moisture content meter.

The 2-ethoxyethanol-replaced slurry was dried with a spray drier (B-290 manufactured by Buchi Labortechnik AG, Japan) at a feed rate of 5 mL/min and inlet and outlet temperatures of 150° C. and 100° C., respectively, to obtain a powder containing zirconia particles and a fluorescent agent.

By uniaxial pressing, the powder was formed into a plate shape measuring 80 mm×40 mm×10 mm in size, and a disc shape measuring 15 mm in diameter and 1.5 mm in thickness. These were then subjected to cold isostatic pressing (CIP; 170 MPa pressure) to obtain zirconia shaped bodies of increased density. These zirconia shaped bodies were calcined at 700° C. for 2 hours under ordinary pressure to obtain zirconia calcined bodies. The zirconia calcined bodies were sintered at 1,100° C. for 2 hours under ordinary pressure to obtain zirconia sintered bodies. The zirconia sintered bodies obtained were white in color, and had fluorescence. The measurement results are presented in Table 2.

A zirconia calcined body produced in the same manner as described above was cut into shapes of crowns for maxillary central incisor and mandibular first molar using a milling device (Katana H-18 manufactured by Kuraray Noritake Dental Inc.). These were then sintered at 1,100° C. for 2 hours under ordinary pressure to obtain crown-shaped dental prostheses having fluorescence.

Example 9

Isopropanol was added to a water-based zirconia slurry containing 5 mol % yttria (MELox Nanosize 5Y manufactured by MEL Chemicals; average primary particle diameter of zirconia particles=13 nm, zirconia concentration=23 mass %) in 9 times the volume of the zirconia slurry. The mixture was placed in a centrifuge tube, thoroughly mixed, and centrifuged at 4,000 rpm for 10 minutes. After confirming sedimentation of a white substance, the supernatant was removed, and isopropanol was added again. The mixture was thoroughly mixed, and centrifuged at 4,000 rpm for 10 minutes. The supernatant was removed after confirming sedimentation of a white substance, and methanol was added to make the volume of the mixture the same as the volume of the zirconia slurry used. The mixture was then thoroughly mixed to obtain a methanol-replaced slurry. The methanol-replaced slurry had a residual moisture content of 0.08 mass % as measured with a Karl Fisher moisture content meter.

A dilute nitric acid solution of bismuth nitrate was added to the methanol-replaced slurry so that the resulting mixture had a concentration of 0.02 mass % in terms of an oxide of bismuth ($Bi_2O_3$) relative to the mass of zirconia. This produced a slurry containing zirconia particles and a fluorescent agent. The slurry was dried with a spray drier (B-290 manufactured by Buchi Labortechnik AG, Japan) at a feed rate of 5 mL/min and inlet and outlet temperatures of 150° C. and 100° C., respectively, to obtain a powder containing zirconia particles and a fluorescent agent.

A zirconia shaped body, a zirconia calcined body, and a zirconia sintered body were obtained in the same manner as in Example 8, except that the powder produced above was used in place of the powder used in Example 8. The zirconia sintered body obtained was white in color, and had fluorescence. The measurement results are presented in Table 2.

Example 10

An aqueous solution of bismuth hydroxide was added to 100 parts by mass of a water-based zirconia slurry containing 8 mol % yttria (MELox Nanosize 8Y manufactured by MEL Chemicals; average primary particle diameter of zirconia particles=13 nm, zirconia concentration=23 mass %) so that the resulting mixture had a concentration of 0.02 mass % in terms of an oxide of bismuth ($Bi_2O_3$) relative to the mass of zirconia. This was followed by a dispersion medium replacement procedure, in which 50 parts by mass of 2-ethoxyethanol was added, and concentrated to make the total amount 100 parts by mass, using a rotary evaporator. The dispersion medium replacement procedure was repeated 4 times to obtain a 2-ethoxyethanol-replaced slurry. The 2-ethoxyethanol-replaced slurry had a residual moisture content of 0.04 mass % as measured with a Karl Fisher moisture content meter.

The 2-ethoxyethanol-replaced slurry was dried with a spray drier (B-290 manufactured by Buchi Labortechnik AG, Japan) at a feed rate of 5 mL/min and inlet and outlet temperatures of 150° C. and 100° C., respectively, to obtain a powder containing zirconia particles and a fluorescent agent.

A zirconia shaped body, a zirconia calcined body, and a zirconia sintered body were obtained in the same manner as in Example 8, except that the powder produced above was used in place of the powder used in Example 8. The zirconia sintered body obtained was white in color, and had fluorescence. The measurement results are presented in Table 2.

Example 11

A dilute nitric acid solution of bismuth nitrate was added to a water-based zirconia slurry containing 5 mol % yttria (MELox Nanosize 5Y manufactured by MEL Chemicals; average primary particle diameter of zirconia particles=13 nm, zirconia concentration=23 mass %) so that the resulting mixture had a concentration of 0.02 mass % in terms of an oxide of bismuth ($B_2O_3$) relative to the mass of zirconia. Thereafter, isopropanol was added in 9 times the volume of the zirconia slurry used. The mixture was placed in a centrifuge tube, thoroughly mixed, and centrifuged at 4,000 rpm for 10 minutes. After confirming sedimentation of a white substance, the supernatant was removed, and isopropanol was added again. The mixture was thoroughly mixed, and centrifuged at 4,000 rpm for 10 minutes. The supernatant was removed after confirming sedimentation of a white substance, and tert-butyl alcohol was added to make the volume of the mixture the same as the volume of the zirconia slurry used. The mixture was then thoroughly mixed to obtain a tert-butyl alcohol-replaced slurry. The tert-butyl alcohol-replaced slurry had a residual moisture content of 0.05 mass % as measured with a Karl Fisher moisture content meter.

The tert-butyl alcohol-replaced slurry was transferred to an aluminum vat, and immersed in liquid nitrogen in a Dewar flask to freeze. The frozen tert-butyl alcohol-replaced slurry was allowed to stand in a freeze drier that had been precooled to −40° C. The pressure inside the freeze drier was then reduced to 130 Pa or less with a vacuum pump to bring the temperature inside the freeze drier to −10° C. The internal temperature was confirmed by inserting temperature sensors inside and outside of the aluminum vat. After the temperature inside the freeze drier had stabilized at −10° C. for 72 hours, the temperature difference inside and outside of the aluminum vat was confirmed to be within 5° C., and the temperature inside the freeze drier was brought to 30° C. After being allowed to stand for 24 hours, the inside of the freeze drier was released from the reduced pressure to obtain a powder containing zirconia particles and a fluorescent agent.

A zirconia shaped body, a zirconia calcined body, and a zirconia sintered body were obtained in the same manner as in Example 8, except that the powder produced above was used in place of the powder used in Example 8. The zirconia sintered body obtained was white in color, and had fluorescence. The measurement results are presented in Table 2.

oxide of bismuth ($Bi_2O_3$) relative to the mass of zirconia. Thereafter, isopropanol was added in 9 times the volume of the zirconia slurry used. The mixture was placed in a centrifuge tube, thoroughly mixed, and centrifuged at 4,000 rpm for 10 minutes. After confirming sedimentation of a white substance, the supernatant was removed, and isopropanol was added again. The mixture was thoroughly mixed, and centrifuged at 4,000 rpm for 10 minutes. The supernatant was removed after confirming sedimentation of a white substance, and methanol was added to make the volume of the mixture the same as the volume of the zirconia slurry used. The mixture was then thoroughly mixed to obtain a methanol-replaced slurry.

The methanol-replaced slurry produced was subjected to supercritical drying with a supercritical drier using the following procedure. Specifically, the methanol-replaced slurry was placed in a pressure vessel, and the pressure vessel was coupled to a supercritical carbon dioxide extraction device. After checking that there is no pressure leak, the pressure vessel, with a preheating tube, was immersed in a water bath that had been heated to 60° C. The slurry was then allowed to stand for 10 minutes to stabilize after being heated to 80° C. and pressurized to 25 MPa. Thereafter, carbon dioxide and entrainer methanol were introduced under predetermined conditions (temperature: 80° C., pressure: 25 MPa, carbon dioxide flow rate: 10 mL/min, entrainer (methanol) flow rate: 1.5 mL/min). The feeding of methanol was discontinued after an elapsed time period of 2 hours, without stopping the carbon dioxide feed. After 2 hours with the sole supply of carbon dioxide, the feeding of carbon dioxide was stopped, and the pressure was gradually brought back to ordinary pressure from 25 MPa over a time period of about 20 minutes at a maintained temperature of 80° C. The pressure vessel was then taken out of the water bath, and cooled to ordinary temperature. The processed specimen was collected by opening the container, and a powder containing zirconia particles and a fluorescent agent was obtained.

A zirconia shaped body, a zirconia calcined body, and a zirconia sintered body were obtained in the same manner as in Example 8, except that the powder produced above was used in place of the powder used in Example 8. The zirconia

TABLE 2

| | | Example | | | | | |
|---|---|---|---|---|---|---|---|
| Zirconia sintered body | | 6 | 7 | 8 | 9 | 10 | 11 |
| Content of fluorescent agent(*1) | Mass % | 0.02 | 0.02 | 0.02 | 0.02 | 0.02 | 0.02 |
| Content of colorant (*1) | Mass % | 0.02 | — | — | — | — | — |
| Content of yttria (*2) | Mol % | 5 | 5 | 5 | 5 | 8 | 5 |
| Crystal grain size | nm | 119 | 108 | 114 | 115 | 114 | 111 |
| Three-point flexural strength | MPa | 808 | 820 | 801 | 742 | 600 | 652 |
| Light transmittance (wavelength 700 nm, thickness 0.5 mm) | % | 47 | 50 | 46 | 42 | 51 | 41 |
| Fraction of cubical crystal | % | 100 | 100 | 100 | 100 | 100 | 100 |
| Fraction of monoclinic crystal after hot-water treatment | % | 0 | 0 | 0 | 0 | 0 | 0 |

(*1) Content relative to the mass of zirconia (the content is in terms of an oxide of metallic element)
(*2) Fraction of number of moles of yttria with respect to total number of moles of zirconia and yttria

Example 12

A dilute nitric acid solution of bismuth nitrate was added to a water-based zirconia slurry containing 5 mol % yttria (MELox Nanosize 5Y manufactured by MEL Chemicals; average primary particle diameter of zirconia particles=13 nm, zirconia concentration=23 mass %) so that the resulting mixture had a concentration of 0.02 mass % in terms of an sintered body obtained was white in color, and had fluorescence. The measurement results are presented in Table 3.

Example 13

A 1.0-L mixed aqueous solution of 0.62 mol/L zirconium oxychloride and 0.065 mol/L yttrium chloride, and 0.5 L of a 1.9 mol/L aqueous solution of sodium hydroxide were separately prepared.

After pouring 1.0 L of purified water into a precipitation vessel, the mixed aqueous solution and the sodium hydroxide aqueous solution were simultaneously poured into the vessel to obtain a slurry through coprecipitation of zirconium oxychloride and yttrium chloride. The slurry was filtered and washed, and purified water was added to obtain a 1.0-L slurry having a solid content of 5.0 mass % (a concentration of zirconia and yttria). After adding 22.2 g of acetic acid to the slurry, a hydrothermal treatment was conducted at 200° C. for 3 hours to obtain a zirconia slurry. The zirconia particles contained in the zirconia slurry had an average primary particle diameter of 18 nm.

A dilute nitric acid solution of bismuth nitrate was added to 100 parts by mass of the zirconia slurry so that the resulting mixture had a concentration of 0.02 mass % in terms of an oxide of bismuth ($Bi_2O_3$) relative to the mass of zirconia. This was followed by a dispersion medium replacement procedure, in which 50 parts by mass of 2-ethoxyethanol was added, and concentrated to make the total amount 100 parts by mass, using a rotary evaporator. The dispersion medium replacement procedure was repeated 4 times to obtain a 2-ethoxyethanol-replaced slurry. The 2-ethoxyethanol-replaced slurry had a residual moisture content of 0.06 mass % as measured with a Karl Fisher moisture content meter.

A zirconia particle- and fluorescent agent-containing powder, a zirconia shaped body, a zirconia calcined body, and a zirconia sintered body were obtained in the same manner as in Example 12, except that the 2-ethoxyethanol-replaced slurry produced above was used in place of the methanol-replaced slurry. The zirconia sintered body obtained was white in color, and had fluorescence. The measurement results are presented in Table 3.

Example 14

An aqueous solution of nickel(II) nitrate was added to 100 parts by mass of a water-based zirconia slurry containing 5 mol % yttria (MELox Nanosize 5Y manufactured by MEL Chemicals; average primary particle diameter of zirconia particles=13 nm, zirconia concentration=23 mass %) so that the resulting mixture had a concentration of 0.02 mass % in terms of an oxide of nickel(II) (NiO) relative to the mass of zirconia. A dilute nitric acid solution of bismuth nitrate was then added to the mixture so that the resulting mixture had a concentration of 0.02 mass % in terms of an oxide of bismuth ($Bi_2O_3$) relative to the mass of zirconia. This was followed by a dispersion medium replacement procedure, in which 50 parts by mass of 2-ethoxyethanol was added, concentrated to make the total amount 100 parts by mass, using a rotary evaporator. The dispersion medium replacement procedure was repeated 4 times to obtain a 2-ethoxyethanol-replaced slurry. The 2-ethoxyethanol-replaced slurry had a residual moisture content of 0.02 mass % as measured with a Karl Fisher moisture content meter.

A zirconia particle-, fluorescent agent-, and colorant-containing powder, a zirconia shaped body, a zirconia calcined body, and a zirconia sintered body were obtained in the same manner as in Example 12, except that the 2-ethoxyethanol-replaced slurry produced above was used in place of the methanol-replaced slurry. The zirconia sintered body obtained was red in color, and had fluorescence. The measurement results are presented in Table 3.

Example 15

An aqueous solution of europium acetate was added to a water-based zirconia slurry containing 5 mol % yttria (MELox Nanosize 5Y manufactured by MEL Chemicals; average primary particle diameter of zirconia particles=13 nm, zirconia concentration=23 mass %) so that the resulting mixture had a concentration of 0.02 mass % in terms of an oxide of europium ($Eu_2O_3$) relative to the mass of zirconia. Thereafter, isopropanol was added in 9 times the volume of the zirconia slurry used. The mixture was placed in a centrifuge tube, thoroughly mixed, and centrifuged at 4,000 rpm for 10 minutes. After confirming sedimentation of a white substance, the supernatant was removed, and isopropanol was added again. The mixture was thoroughly mixed, and centrifuged at 4,000 rpm for 10 minutes. The supernatant was removed after confirming sedimentation of a white substance, and methanol was added to make the volume of the mixture the same as the volume of the zirconia slurry used. The mixture was then thoroughly mixed to obtain a methanol-replaced slurry. The methanol-replaced slurry had a residual moisture content of 0.08 mass % as measured with a Karl Fisher moisture content meter.

A zirconia particle- and fluorescent agent-containing powder, a zirconia shaped body, a zirconia calcined body, and a zirconia sintered body were obtained in the same manner as in Example 12, except that the methanol-replaced slurry produced above was used in place of the methanol-replaced slurry used in Example 12. The zirconia sintered body obtained was white in color, and had fluorescence. The measurement results are presented in Table 3.

A zirconia calcined body produced in the same manner as described above was cut into shapes of crowns for maxillary central incisor and mandibular first molar using a milling device (Katana H-18 manufactured by Kuraray Noritake Dental Inc.). These were then sintered at 1,100° C. for 2 hours under ordinary pressure to obtain crown-shaped dental prostheses having fluorescence.

Example 16

A composition containing zirconia particles, a fluorescent agent, and a resin was obtained by adding and kneading 30 parts by mass of polyvinyl alcohol into 50 parts by mass of a zirconia particle- and fluorescent agent-containing powder obtained in the same manner as in Example 12.

The composition was formed into a zirconia shaped body by injection molding using an injection molding machine. The zirconia shaped body was calcined at 700° C. for 2 hours under ordinary pressure to obtain a zirconia calcined body. The zirconia calcined body was sintered at 1,100° C. for 2 hours under ordinary pressure to obtain a zirconia sintered body. The zirconia sintered body obtained was white in color, and had fluorescence. The measurement results are presented in Table 3.

Example 17

In a dark room, 30 parts by mass of 2-hydroxyethylmethacrylate, 5 parts by mass of 10-methacryloyloxydecyl dihydrogen phosphate, and 1 part by mass of 2,4,6-trimethylbenzoyldiphenylphosphine oxide (photopolymerization initiator) were added and kneaded into 50 parts by mass of a zirconia particle- and fluorescent agent-containing powder obtained in the same manner as in Example 12. This produced a composition containing zirconia particles, a fluorescent agent, a polymerizable monomer, and a photopolymerization initiator.

The composition was charged into a mold, and polymerized with a UV irradiator to obtain a zirconia shaped body. The zirconia shaped body was calcined at 700° C. for 2 hours under ordinary pressure to obtain a zirconia calcined body. The zirconia calcined body was sintered at 1,100° C. for 2 hours under ordinary pressure to obtain a zirconia sintered body. The zirconia sintered body obtained was white in color, and had fluorescence. The measurement results are presented in Table 3.

Example 18

(1) Eighty parts by mass of propylene glycol monomethyl ether acetate (commonly known as "PGMEA") as organic solvent, and six parts by mass of 2-(2-(2-methoxyethoxy)ethoxy)acetic acid (commonly known as "MEEAA") as surface treatment agent were added to 100 parts by mass of a water-based zirconia slurry containing 5 mol % yttria (MELox Nanosize 5Y manufactured by MEL Chemicals; average primary particle diameter of zirconia particles=13 nm, zirconia concentration=23 mass %). The mixture was transferred to a round-bottom flask, and about 60 parts by mass of water and PGMEA was removed under reduced pressure, using a rotary evaporator. After adding toluene to the residue, the same removal procedure was carried out under reduced pressure to remove water, PGMEA, and toluene in the form of an azeotrope. The azeotrope removal procedure by addition of toluene to the residue was repeated several times to thoroughly remove water, and a transparent, fluidic slurry containing 45 mass % zirconia particles was obtained. The main component of the dispersion medium in the slurry is PGMEA.

(2) To 20 parts by mass of the slurry obtained above were added 4 parts by mass of triethylene glycol dimethacrylate (commonly known as "TEGDMA"), 4 parts by mass of 2,2,4-trimethylhexamethylene bis(2-carbamoyloxyethyl)dimethacrylate [a substance obtained after adding 2-hydroxyethylmethacrylate to 2,2,4-trimethylhexamethylenediisocyanate in a molar ratio of 2:1; commonly known as "UDMA"], and 0.6 parts by mass of 2,4,6-trimethylbenzoyldiphenylphosphine oxide (commonly known as "TPO"; a photopolymerization initiator). These were uniformly mixed and dissolved. A dilute hydrochloric acid solution of bismuth acetate oxide as fluorescent agent was then mixed into the mixture so that the resulting mixture had a concentration of 0.01 mass % in terms of an oxide of bismuth ($Bi_2O_3$) relative to the mass of zirconia. This produced a composition containing zirconia particles, a fluorescent agent, a polymerizable monomer, and a photopolymerization initiator. The composition had a viscosity at 25° C. of 2,500 mPa·s (as measured with an E-type viscometer).

(3) The composition was poured into a polytetrafluoroethylene mold (measuring 3 cm×3 cm in size with a depth of 5 mm), and polymerized and cured under light applied for 5 minutes with a dental photo-polymerization irradiator (α-Light III manufactured by Morita Mfg. Corp.). The cured product was allowed to stand at room temperature in air for 3 days to dry, and released from the mold to obtain a zirconia shaped body.

(4) The zirconia shaped body produced was calcined under ordinary pressure to obtain a zirconia calcined body, using an electric furnace (Katana F manufactured by Kuraray Noritake Dental Inc.). The calcination was conducted by increasing temperature from room temperature to 200° C. at a rate of 0.3° C./min, 200° C. to 260° C. at a rate of 0.1° C./min, and 260° C. to 400° C. at a rate of 0.3° C./min. The zirconia calcined body was then put back in the electric furnace, and was sintered by increasing temperature to 1,050° C. at a rate of 60° C./hour under ordinary pressure to obtain a compact zirconia sintered body. The zirconia sintered body obtained was white in color, and had fluorescence. The measurement results are presented in Table 3.

TABLE 3

| Zirconia sintered body | | Example | | | | | | |
|---|---|---|---|---|---|---|---|---|
| | | 12 | 13 | 14 | 15 | 16 | 17 | 18 |
| Content of fluorescent agent(*1) | Mass % | 0.02 | 0.02 | 0.02 | 0.02 | 0.02 | 0.02 | 0.01 |
| Content of colorant (*1) | Mass % | — | — | 0.02 | — | — | — | — |
| Content of yttria (*2) | Mol % | 5 | 5 | 5 | 5 | 5 | 5 | 5 |
| crystal grain size | nm | 110 | 118 | 119 | 112 | 118 | 118 | 118 |
| Three-point flexural strength | MPa | 802 | 636 | 802 | 802 | 720 | 692 | 750 |
| Light transmittance (wavelength 700 nm, thickness 0.5 mm) | % | 48 | 42 | 43 | 46 | 46 | 46 | 47 |
| Fraction of cubical crystal | % | 100 | 100 | 100 | 100 | 100 | 100 | — |
| Fraction of monoclinic crystal after hot-water treatment | % | 0 | 0 | 0 | 0 | 0 | 0 | — |

(*1) Content relative to the mass of zirconia (the content is in terms of an oxide of metallic element)
(*2) Fraction of number of moles of yttria with respect to total number of moles of zirconia and yttria

The invention claimed is:

1. A zirconia sintered body comprising
a fluorescent agent,
wherein the zirconia sintered body comprises 4.5 to 9.0 mol % yttria, and has a crystal grain size of 1.80 nm or less, and a three-point flexural strength of 500 MPa or more.

2. The zirconia sintered body according to claim 1,
wherein the fluorescent agent contains a metallic element, and
the zirconia sintered body comprises the fluorescent agent in an amount of 0.001 to 1 mass % in terms of an oxide of the metallic element relative to a mass of zirconia.

3. The zirconia sintered body according to claim 1,
wherein the zirconia sintered body has a transmittance of 40% or more for light of 700 nm wavelength through a thickness of 0.5 mm.

4. The zirconia sintered body according to claim 1,
wherein the zirconia sintered body comprises a cubical crystal as a predominant crystal phase.

5. A method for producing the zirconia sintered body of claim 1, comprising
a step of sintering a zirconia shaped body under ordinary pressure,
wherein the zirconia shaped body comprises a fluorescent agent, and
wherein the zirconia shaped body comprises 4.5 to 9.0 mol % yttria, and wherein the zirconia shaped body satisfies the following properties when subjected to the following conditions:
(i) has a three-point flexural strength of 500 MPa or more after being sintered at 1,100° C. for 2 hours under ordinary pressure, and (ii) a crystal grain size of 180 nm or less after being sintered at 1,100° C. for 2 hours under ordinary pressure.

6. A method for producing the zirconia sintered body of claim 1, comprising
sintering a zirconia calcined body under ordinary pressure,
wherein the zirconia sintered body comprises a fluorescent agent, and
wherein the zirconia sintered body comprises 4.5 to 9.0 mol % yttria, and has a crystal grain size of 180 nm or less, and a three-point flexural strength of 500 MPa or more.

7. A zirconia shaped body comprising
a fluorescent agent,
wherein the zirconia shaped body comprises 4.5 to 9.0 mol % yttria, and has a three-point flexural strength of 500 MPa or ore after being sintered at 1,100° C. for 2 hours under ordinary pressure, and a crystal grain size of 180 nm or less after being sintered at 1,100° C. for 2 hours under ordinary pressure.

8. The zirconia shaped body according to claim 7,
wherein the fluorescent agent comprises a metallic element, and
the zirconia shaped body comprises the fluorescent agent in an amount of 0.001 to 1 mass % in terms of an oxide of the metallic element relative to a mass of zirconia.

9. The zirconia shaped body according to claim 7,
wherein the zirconia shaped body has a transmittance of 40% or more for light of 700 nm wavelength through a thickness of 0.5 mm after being sintered at 1,100° C. for 2 hours under ordinary pressure.

10. A method for producing the zirconia shaped body of claim 7, comprising:
mixing a zirconia particle-containing slurry with a fluorescent agent to obtain zirconia particles comprising the fluorescent agent; and
a shaping step of shaping the zirconia particles,
wherein the zirconia particles comprise 4.5 to 9.0 mol % yttria, and have an average primary particle diameter of 20 nm or less.

11. The method according to claim 10,
wherein the shaping step is a step of slip casting a slurry comprising zirconia particles and a fluorescent agent.

12. The method according to claim 10,
wherein the shaping step is a step of gel casting a slurry comprising zirconia particles and a fluorescent agent.

13. The method according to claim 10,
wherein the shaping step is a step of pressing a powder comprising zirconia particles and a fluorescent agent.

14. The method according to claim 10, wherein the shaping is a step of shaping a composition comprising zirconia particles, a fluorescent agent, and a resin.

15. The method according to claim 10, wherein the shaping step comprises polymerizing a composition comprising zirconia particles, a fluorescent agent, and a polymerizable monomer.

16. The method according to claim 15, wherein the shaping step is a stereolithography process.

17. A zirconia calcined body comprising
a fluorescent agent,
wherein the zirconia calcined body comprises 4.5 to 9.0 mol % yttria, and has a three-point flexural strength of 500 MPa or more after being sintered at 1,100° C. for 2 hours under ordinary pressure, and a crystal grain size of 180 nm or less after being sintered at 1,100° C. for 2 hours under ordinary pressure.

18. The zirconia calcined body according to claim 17,
wherein the fluorescent agent contains a metallic element, and the zirconia calcined body comprises the fluorescent agent in an amount of 0.001 to 1 mass % in terms of an oxide of the metallic element relative to a mass of zirconia.

19. The zirconia calcined body according to claim 17,
wherein the zirconia calcined body has a transmittance of 40% or more for light of 700 nm wavelength through a thickness of 0.5 mm after being sintered at 1,100° C. for 2 hours under ordinary pressure.

20. A method for producing the zirconia calcined body of claim 17, comprising
a step of calcining a zirconia shaped body, wherein the zirconia shaped body comprises a fluorescent agent, and
wherein the zirconia shaped body comprises 4.5 to 9.0 mol % yttria, and has a three-point flexural strength of 500 MPa or more after being sintered at 1,100° C. tor hours under ordinary pressure, and a crystal grain size of 180 nm or less after being sintered at 1,100° C. for 2 hours under ordinary pressure.

21. The method according to claim 20,
wherein the calcination is carried out between 300° C. or more and less than 900° C.

* * * * *